United States Patent [19]

Perrone et al.

[11] 4,358,448

[45] Nov. 9, 1982

[54] N-SUBSTITUTED THIAZOLYL DERIVATIVES OF OXY-IMINO-SUBSTITUTED CEPHALOSPORINS USEFUL AS ANTI-BACTERIAL AGENTS

[75] Inventors: Ettore Perrone; Giuliano Nannini, both of Bresso; Marco Alpegiani, Caminata Val Tidone; Franco Giudici, Arese; Giuseppe Meinardi, Milan, all of Italy

[73] Assignee: Farmitalia Carlo Erba S.p.A., Milan, Italy

[21] Appl. No.: 206,078

[22] Filed: Nov. 12, 1980

[30] Foreign Application Priority Data

Dec. 7, 1979 [GB] United Kingdom ................. 7942269

[51] Int. Cl.$^3$ ..................... A61K 31/54; C07D 501/00
[52] U.S. Cl. .................................... 424/246; 544/22; 544/27; 544/28; 542/416
[58] Field of Search ....................... 544/27, 25, 28, 22; 424/246; 542/416

[56] References Cited

PUBLICATIONS

Derwent Farmdoc 70716Y–Abstract of Belgian Pat. 853,073 (2/77).
Derwent Farmdoc 76253A–Abstract of Belgian Pat. 866,038 (10/78).
Derwent Farmdoc 66853Y–Abstract of Belgian Pat. 852,427 (9/77).
Derwent Farmdoc 74147Y–Abstract of Belgian Pat. 853,545 (10/77).
Derwent Farmdoc 00060A–Abstract of Belgian Pat. 856,045 (2/77).
Derwent Farmdoc 46081W–Abstract of Belgian Pat. 823,861 (6/75).
Derwent Farmdoc 37977B–Abstract of Japan Kokai 44695/79 (1/78).
Derwent Farmdoc 79405B–Abstract of European Pat. 4956 (10/78).
Derwent Farmdoc 50298X–Abstract of German Offenlegungsschrift 2,556,736 (6/76).

*Primary Examiner*—Nicky Chan
*Attorney, Agent, or Firm*—Murray and Whisenhunt

[57] ABSTRACT

Derivatives of N-substituted thiazolyl oxy-imino-substituted cephalosporins, such as, for instance, the compound 7β-[2-(2-imino-3-hydroxy-4-thiazolinyl)-2-methoxy-imino-acetamino]-3-[(tetrazolo[1,5-b]pyridazin-6-yl)-thiomethyl]-3-cephem-4-carboxylic acid, are disclosed. The disclosed compounds have high anti-bacterial activity against Gram-positive and Gram-negative bacteria normally susceptible to cephalosporins.

11 Claims, No Drawings

N-SUBSTITUTED THIAZOLYL DERIVATIVES OF OXY-IMINO-SUBSTITUTED CEPHALOSPORINS USEFUL AS ANTI-BACTERIAL AGENTS

The present invention relates to derivatives of N-substituted thiazolyl oxy-imino-substituted cephalosporins, to a process for their preparation and to pharmaceutical and veterinary compositions containing them.

The invention provides compounds of the general formula (I):

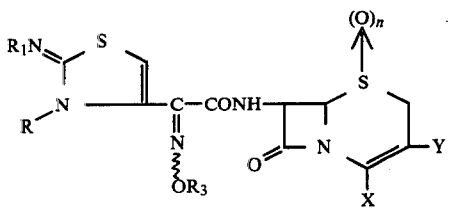

wherein
R is (1) —$OR_2$ in which $R_2$ is a hydrogen atom or a saturated or unsaturated $C_1$–$C_6$ branched or straight chain aliphatic hydrocarbon group which is unsubstituted or substituted by a substituent selected from the group consisting of (a) cyano; (b) —$COOR_4$ in which $R_4$ is hydrogen, $C_1$–$C_6$ alkyl, or a carboxy-protecting group and (c)

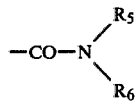

in which each of the groups $R_5$ and $R_6$, which may be the same or different, represents a hydrogen atom, a $C_1$–$C_6$ alkyl or an aliphatic acyl group or, when $R_5$ is hydrogen, $R_6$ may be also an amino-protecting group or (2)

wherein $R_5$ and $R_6$ are as defined above;
$R_1$ represents a hydrogen atom or an amino-protecting group;
$R_3$ represents a hydrogen atom, a hydroxy-protecting group or a branched or straight chain saturated or unsaturated $C_1$–$C_6$ aliphatic hydrocarbon group, which may be unsubstituted or substituted by one or more substituents selected from (a') hydroxy; (b') cyano; (c') $C_1$–$C_6$ alkyl, (d')

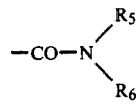

in which $R_5$ and $R_6$ are as defined above; (e') —$COOR_7$ in which $R_7$ is hydrogen, $C_1$–$C_6$ alkyl, aryl, indanyl, acetoxymethyl or a carboxy-protecting group or (f') halo-$C_1$–$C_6$ alkyl;
n is zero, 1 or 2;
Y is hydrogen; halogen; hydroxy; $C_1$–$C_6$ alkoxy; $C_1$–$C_6$ alkyl or a group —$CH_2$—Z in which Z is (1) —OCOCH$_3$ or (2)

where R' is hydrogen, $C_1$–$C_6$ alkyl, carboxy, cyano or carbamoyl; or (3) —S—Het, wherein Het represents (A) a pentatomic or hexatomic heteromonocyclic ring containing at least one double bond and at least one heteroatom selected from N, S, and O, which ring is unsubstituted or substituted by one or more substituents selected from:
(a'') hydroxy, $C_1$–$C_6$ alkoxy, halogen, $C_2$–$C_6$ aliphatic acyl;
(b'') $C_1$–$C_6$ alkyl which is unsubstituted or substituted by one or more substituents selected from hydroxy and halogen;
(c'') $C_2$–$C_6$ alkenyl which is unsubstituted or substituted by one or more substituents selected from hydroxy and halogen;
(d'') —S—$R_8$ wherein $R_8$ is hydrogen or $C_1$–$C_6$ alkyl or —S—$CH_2$—$COOR_4$ wherein $R_4$ is as defined above;
(e'') —($CH_2$)m—$COOR_4$ or —CH=CH—$COOR_4$ wherein m is 0, 1, 2 or 3 and $R_4$ is as defined above; —($CH_2$)m—CN or —($CH_2$)m—$CONH_2$ wherein m is as defined above —($CH_2$)m—$SO_3H$ wherein m is as defined above; or
(f'')

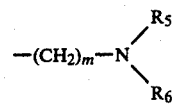

wherein m, $R_5$ and $R_6$ are as defined above, or
(B) a heterobicyclic ring containing at least two double bonds wherein each of the condensed heteromonocyclic rings, being the same or different, is a pentatomic or hexatomic heteromonocyclic ring containing at least a heteroatom selected from N, S and O, the heterobicyclic ring being unsubstituted or substituted by one or more substituents selected from a'', b'', c'', d'', e'' and f'' above; and
X is a free or esterified carboxy group; and the pharmaceutically and veterinarily acceptable salts thereof.

The above definition of the compounds of the present invention includes within its scope all possible isomers of the compounds e.g. syn and anti-isomers, cis and trans isomers and optical isomers, and their mixtures, the metabolites provided with antibacterial activity and the metabolic precursors of the compounds of formula (I).

In the formulae of the invention the wavy line ( $\xi$ ) means that the oxy-imino group may be both in the syn and in the anti-configuration.

As already said, both the single syn and anti-isomers of the compounds of formula (I) and their mixtures are included in the scope of the invention.

The chain linked to the carbon atom in the 7-position is always a 7β-chain.

When in the compound of formula (I) R is —OH the 7β-chain may take either or both of the two following tautomeric forms (IA) and (IB)

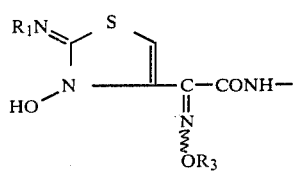

(thiazoline form)

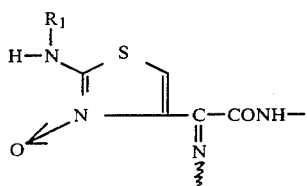

(thiazole form)

This invention includes both the compounds of formula (I) wherein the 7β-chain is in the thiazoline form (IA) and those wherein the 7β-chain is in the thiazole form (IB) as well as the mixtures thereof.

The compounds of formula (I) where n is 1 are sulphoxides and these may be in the R or S configuration. When n is 2 the resulting compounds are sulphones.

When X is an esterified carboxy group, it is preferably a group of formula —COOM, wherein M is one of the radicals

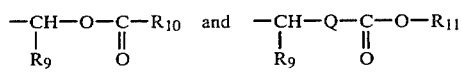

wherein $R_9$ is hydrogen or $C_1$–$C_6$ alkyl; Q is —O— or —NH—; $R_{10}$ is an alkyl group (e.g. $C_1$–$C_6$ alkyl) or a basic group, in particular an alkyl (e.g. $C_1$–$C_6$ alkyl) or aralkyl (e.g. benzyl) group substituted by at least an amino group, which in turn, may be unsubstituted or substituted, e.g. $R_{10}$ is alkyl—NH—$CH_3$, aralkyl—N-H—$CH_3$,

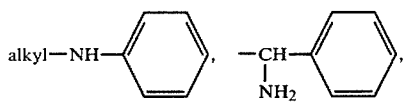

—$CH_2$—$NH_2$; $R_{11}$ is an alkyl group, in particular a $C_1$–$C_6$ alkyl group, e.g. methyl, propyl or isopropyl; an aryl group, in particular phenyl; a cycloalkyl group, in particular cyclopentyl, cyclohexyl and cycloheptyl; a heteromonocyclic ring, e.g. pyridyl; a bicyclic ring, e.g. indanyl; an aralkyl group, e.g. benzyl.

When $R_1$ is an amino-protecting group it is, for example, one of the protecting groups usually employed in the chemistry of peptides, e.g. formyl; an optionally halo-substituted $C_2$–$C_6$ aliphatic acyl, preferably chloroacetyl or dichloroacetyl; tert-butoxycarbonyl; p-nitrobenzyl-oxy-carbonyl or trityl.

When $R_2$ is a $C_1$–$C_6$ aliphatic hydrocarbon group it is preferably $C_1$–$C_6$ alkyl, especially $C_1$–$C_3$ alkyl or $C_2$–$C_3$ alkenyl.

When $R_3$ is a hydroxy-protecting group it may be, for example, a formyl acetyl, chloroacetyl, dichloroacetyl, trifluoroacetyl, tetrahydropyranyl, trityl or silyl group, especially trimethylsilyl or dimethyl-tert-butylsilyl.

A carboxy protecting group may be one of the protecting groups usually employed in the chemistry of the peptides, for example, tert-butyl, benzhydryl, p-methoxybenzyl, p-nitrobenzyl, trityl, trialkylsilyl and the like.

An aliphatic acyl group is preferably a $C_2$–$C_6$ aliphatic acyl preferably $C_2$–$C_6$ alkanoyl, e.g. acetyl.

A halo-$C_1$–$C_6$-alkyl group is preferably a trihalo-$C_1$–$C_6$-alkyl group, in particular trifluoromethyl. An aryl group is preferably a phenyl group.

The pharmaceutically and veterinarily acceptable salts of the compounds of formula (I) are those either with inorganic acids, such as hydrochloric and sulphuric acid, or with organic acids, such as citric tartaric, malic, maleic, mandelic, fumaric and methanesulphonic acid, or with inorganic bases, such as sodium, potassium, calcium or aluminium hydroxides and alkali metal or alkaline-earth metal carbonates or bicarbonates, or with organic bases, such as organic amines, e.g., lysine, triethylamine, procaine, dibenzylamine, N-benzyl-β-phenetylamine, N,N'-dibenzyl-ethylenediamine, dehydroabietylamine, N-ethylpiperdine, diethanolamine, N-methylglucamine, tris-hydroxymethylaminomethane and the like.

Also internal salts (i.e. zwitterions) are included in the scope of the invention. Preferred compounds of formula (I) are the syn-isomers.

Preferred compounds of the invention are those of formula (I) wherein $R_1$ is hydrogen or an amino-protecting group;
R is -hydroxy; —O—$C_1$–$C_6$ alkyl; —O—$C_2$–$C_4$ alkenyl; —O—$(CH_2)_{m_1}$—$COOR_4$, wherein $R_4$ is as defined above and $m_1$ is 1, 2 or 3; amino; —$NHCH_3$; —$N(CH_3)_2$;

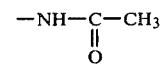

or —NHCOO-tert.butyl;
$R_3$ is hydrogen, $C_1$–$C_6$ alkyl, $C_2$–$C_4$ alkenyl; —$(CH_2)$-$m_1$—COOH,

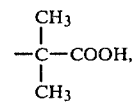

—$(CH_2)_{m_1}$—CN, —$(CH_2)_{m_1}$—$CONH_2$ wherein $m_1$ is as defined above or —CH=CH—COOH;
Y is hydrogen, halogen, (preferably chlorine) hydroxy, $C_1$–$C_6$ alkoxy (preferably methoxy), methyl, —$CH_2$—$OCOCH_3$ or $CH_2$—S—Het wherein Het is:
(1) a tetrazolyl radical, unsubstituted or substituted by $C_1$–$C_3$ alkyl, $C_2$–$C_4$ alkenyl, —$(CH_2)_{m_1}$—$COOR_4$ wherein $m_1$ and $R_4$ are as defined above, —CH=CH—$COOR_4$ wherein $R_4$ is as defined above, —$(CH_2)_{m_1}$—CN; —$(CH_2)_{m_1}$—$CONH_2$ or —$(CH_2)$-$m_1$—$SO_3H$ wherein $m_1$ is as defined above;

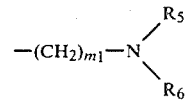

wherein $m_1$, $R_5$ and $R_6$ are as defined above;
(2) a thiadiazolyl radical, unsubstituted or substituted by $C_1$-$C_4$-alkyl, $C_2$-$C_4$ alkenyl, —SH; —SCH$_3$, —SCH$_2$COOH, —(CH$_2$)$_m$—COOH, $$-N\diagup^{R'_5}_{\diagdown R'_6}$$

wherein each of $R_5'$ and $R_6'$ is hydrogen or $C_1$-$C_3$ alkyl and m is as defined above;
(3) a heterobicyclic ring selected from the group consisting of tetrazolopyridazinyl, tetrazolopyrazinyl, thiadiazolopyridazinyl, and triazolopyridazinyl, each optionally substituted by hydroxy, —SH, $$-CO-N\diagup^{R'_5}_{\diagdown R'_6}$$

wherein $R_5'$ and $R_6'$ are as defined above; —COOR$_4$ wherein $R_4$ is as defined above; $C_1$-$C_3$ alkyl; $C_2$-$C_4$ alkenyl; —S—CH$_2$COOR$_4$, —CH$_2$COOR$_4$, or —CH=CH—COOR$_4$ wherein $R_4$ is as defined above; or $$-N\diagup^{R'_5}_{\diagdown R'_6}$$

wherein $R_5'$ and $R_6'$ are as defined above; n is zero; X is a free carboxy group; and the pharmaceutically and veterinarily acceptable salts thereof.

A particularly preferred class of compounds of the invention are the syn-isomers of the compounds of formula (I) wherein:
$R_1$ is hydrogen or an amino-protecting group;
R is hydroxy; —O—C$_1$-C$_6$ alkyl; amino;
$R_3$ is hydrogen; C$_1$-C$_6$ alkyl; C$_2$-C$_4$ alkenyl; —(CH$_2$)$_{m_1}$—COOH wherein $m_1$ is as defined above;

$$\begin{array}{c}CH_3\\|\\-C-COOH\\|\\CH_3\end{array}$$

or —CH=CH—COOH;
Y is hydrogen, halogen, hydroxy, methoxy, methyl, —CH$_2$OCOCH$_3$ or CH$_2$—S—Het, wherein Het is (1) tetrazolyl unsubstituted or substituted by C$_1$-C$_3$ alkyl, C$_2$-C$_4$ alkenyl, —(CH$_2$)$_{m_1}$—COOH, —(CH$_2$)$_{m_1}$—CN or $$-(CH_2)_{m_1}-N\diagup^{R_5}_{\diagdown R_6}$$

wherein $m_1$, $R_5$ and $R_6$ are as defined above; (2) a thiadiazolyl radical, unsubstituted or substituted by methyl, C$_2$-C$_4$ alkenyl; —SH; —SCH$_3$; —SCH$_2$COOH; —(CH$_2$)$_m$—COOH;

$$-N\diagup^{R'_5}_{\diagdown R'_6},$$

wherein $R_5'$, $R_6'$ and m are as defined above; (3) tetrazolopyridazinyl, optionally substituted by hydroxy, —SH, $$-N\diagup^{R'_5}_{\diagdown R'_6},$$

wherein $R_5'$, $R_6'$ and m are as defined above; (3) tetrazolopyridazinyl, optionally substituted by hydroxy, —SH, $$-CON\diagup^{R'_5}_{\diagdown R'_6},$$

wherein $R_5'$ and $R_6'$ are as defined above; —COOR$_4$ wherein $R_4$ is as defined above; C$_1$-C$_3$ alkyl; C$_2$-C$_4$ alkenyl; —CH$_2$COOR$_4$ or —CH=CH—COOR$_4$ wherein $R_4$ is as defined above or $$-N\diagup^{R'_5}_{\diagdown R'_6}$$

wherein $R_5'$ and $R_6'$ are as defined above; n is zero; X is a free carboxy group; and the pharmaceutically and veterinarily acceptable salts thereof.

More particularly preferred compounds of the invention are the syn-isomers of the compounds of formula (I) wherein:
$R_1$ is hydrogen;
R is hydroxy;
$R_3$ is hydrogen, C$_1$-C$_6$ alkyl, C$_2$-C$_4$ alkenyl, —(CH$_2$)$_{m_1}$—COOH wherein $m_1$ is as defined above, $$\begin{array}{c}CH_3\\|\\-C-COOH\\|\\CH_3\end{array}$$

—CH=CH—COOH;
Y is hydrogen, halogen, hydroxy, methoxy, —CH$_2$OCOCH$_3$ or —CH$_2$—S—Het, wherein Het is (1) tetrazolyl unsubstituted or substituted by C$_1$-C$_3$ alkyl, C$_2$-C$_4$ alkenyl, —(CH$_2$)$_{m_1}$—COOH, —(CH$_2$)$_{m_1}$—CN or $$-(CH_2)_{m_1}-N\diagup^{R_5}_{\diagdown R_6}$$

wherein $m_1$, $R_5$ and $R_6$ are as defined above; (2) a thiadiazolyl radical, unsubstituted or substituted by methyl, C$_2$-C$_4$ alkenyl; —SH; —SCH$_3$; —SCH$_2$COOH; —(CH$_2$)$_m$—COOH;

$$-N\diagup^{R'_5}_{\diagdown R'_6},$$

wherein $R_5'$, $R_6'$ and m are as defined above; (3) tetrazolopyridazinyl, optionally substituted by hydroxy, —SH,

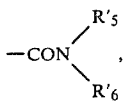

wherein R′₅ and R′₆ are as defined above; —COOR₄ wherein R₄ is as defined above; C₁-C₃ alkyl; C₂-C₄ alkenyl, —CH₂COOR₄ or —CH=CH—COOR₄, wherein R₄ is as defined above or

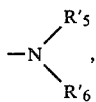

wherein R′₅ and R′₆ are as defined above;

n is zero;

X is a free carboxy group; and the pharmaceutically and veterinarily acceptable salts thereof.

Specific examples of compounds of the invention are the following:

(1) 7β-[2-(2-imino-3-hydroxy-4-thiazolinyl)-2-hydroxy-imino-acetamido]-3-cephem-4-carboxylic acid (syn-isomer);

(2) 7β-[2-(2-imino-3-hydroxy-4-thiazolinyl)-2-methoxy-imino-acetamido]-3-cephem-4-carboxylic acid (syn-isomer);

(3) 7β-[2-(2-imino-3-hydroxy-4-thiazolinyl)-2-methoxy-imino-acetamido]-1(R)-sulphoxide-3-cephem-4-carboxylic acid (syn-isomer);

(4) 7β-[2-(2-imino-3-hydroxy-4-thiazolinyl)-2-methoxy-imino-acetamido]-1(S)-sulphoxide-3-cephem-4-carboxylic acid (syn-isomer);

(5) 7β-[2-(2-imino-3-hydroxy-4-thiazolinyl)-2-methoxy-imino-acetamido]-3-chloro-3-cephem-4-carboxylic acid (syn-isomer);

(6) 7β-[2-(2-imino-3-hydroxy-4-thiazolinyl)-2-methoxy-imino-acetamido]-3-hydroxy-3-cephem-4-carboxylic acid (syn-isomer);

(7) 7β-[2-(2-imino-3-hydroxy-4-thiazolinyl)-2-methoxy-imino-acetamido]-3-methoxy-3-cephem-4-carboxylic acid (syn-isomer);

(8) 7β-[2-(2-imino-3-methoxy-4-thiazolinyl)-2-methoxy-imino-acetamido]-3-cephem-4-carboxylic acid (syn-isomer);

(9) 7β-[2-(2-imino-3-amino-4-thiazolinyl)-2-methoxy-imino-acetamido]-3-cephem-4-carboxylic acid (syn-isomer);

(10) 7β-[2-(2-imino-3-hydroxy-4-thiazolinyl)-2-methoxy-imino-acetamido]-3-acetoxy-methyl-3-cephem-4-carboxylic acid; (syn-isomer);

(11) 7β-[2-(2-imino-3-hydroxy-4-thiazolinyl)-2-methoxy-imino-acetamido]-1(R)-sulphoxide-3-acetoxy-methyl-3-cephem-4-carboxylic acid (syn-isomer);

(12) 7β-[2-(2-imino-3-hydroxy-4-thiazolinyl)-2-methoxy-imino-acetamido]-1(S)-sulphoxide-3-acetoxy-methyl-3-cephem-4-carboxylic acid (syn-isomer);

(13) 7β-[2-(2-imino-3-amino-4-thiazolinyl)-2-methoxy-imino-acetamido]-3-acetoxy-methyl-3-cephem-4-carboxylic acid (syn-isomer);

(14) 7β-[2-(2-imino-3-amino-4-thiazolinyl)-2-methoxy-imino-acetamido]-1(R)-sulphoxide-3-acetoxy-methyl-3-cephem-4-carboxylic acid (syn-isomer);

(15) 7β-[2-(2-imino-3-amino-4-thiazolinyl)-2-methoxy-imino-acetamido]-1(S)-sulphoxide-3-acetoxy-methyl-3-cephem-4-carboxylic acid (syn-isomer);

(16) 7β-[2-(2-imino-3-methoxy-4-thiazolinyl)-2-methoxy-imino-acetamido]-3-acetoxy-methyl-3-cephem-4-carboxylic acid (syn isomer);

(17) 7β-[2-(2-imino-3-methoxy-4-thiazolinyl)-2-methoxy-imino-acetamido]-1(R)-sulphoxide-3-acetoxy-methyl-3-cephem-4-carboxylic acid (syn isomer);

(18) 7β-[2-(2-imino-3-methoxy-4-thiazolinyl)-2-methoxy-imino-acetamido]-1(S)-sulphoxide-3-acetoxy-methyl-3-cephem-4-carboxylic acid (syn isomer);

(19) 7β-[2-(2-imino-3-hydroxy-4-thiazolinyl)-2-methoxy-imino-acetamido]-3-[-(1-methyl-1,2,3,4-tetrazol-5-yl)-thiomethyl]-3-cephem-4-carboxylic acid (syn isomer);

(20) 7β-[2-(2-imino-3-hydroxy-4-thiazolinyl)-2-methoxy-imino-acetamido]-3-[(1-[2-propenyl]-1,2,3,4-tetrazol-5-yl)-thiomethyl]-3-cephem-4-carboxylic acid (syn isomer);

(21) 7β-[2-(2-imino-3-hydroxy-4-thiazolinyl)-2-methoxy-imino-acetamido]-3-[1-(2-cyano ethyl-1,2,3,4-tetrazol-5-yl)-thiomethyl]-3-cephem-4-carboxylic acid (syn isomer);

(22) 7β-[2-(2-imino-3-hydroxy-4-thiazolinyl)-2-methoxy-imino-acetamido]-3-[(5-methyl-1,3,4-thiadiazol-2-yl)-thiomethyl]-3-cephem-4-carboxylic acid (syn isomer);

(23) 7β-[2-(2-imino-3-hydroxy-4-thiazolinyl)-2-methoxy-imino-acetamido]-3-[(5-methyl-mercapto-1,3,4-thiadiazol-2-yl)-thiomethyl]-3-cephem-4-carboxylic acid (syn isomer);

(24) 7β-[2-(2-imino-3-hydroxy-4-thiazolinyl)-2-methoxy-imino-acetamido]-3-[(5-amino-1,3,4-thiadiazol-2-yl)-thiomethyl]-3-cephem-4-carboxylic acid (syn isomer);

(25) 7β-[2-(2-imino-3-hydroxy-4-thiazolinyl)-2-methoxy-imino-acetamido]-3-[(tetrazolo[1,5-b]pyridazin-6-yl)-thiomethyl]-3-cephem-4-carboxylic acid (syn isomer);

(26) 7β-[2-(2-imino-3-hydroxy-4-thiazolinyl)-2-methoxy-imino-acetamido]-3-[(8-amino-tetrazolo[1,5-b]pyridazin-6-yl)-thiomethyl]-3-cephem-4-carboxylic acid (syn isomer);

(27) 7β-[2-(2-imino-3-hydroxy-4-thiazolinyl)-2-methoxy-imino-acetamido]-3-[(8-carboxy-tetrazolo[1,5-b]pyridazin-6-yl)-thiomethyl]-3-cephem-4-carboxylic acid (syn isomer);

(28) 7β-[2-(2-imino-3-hydroxy-4-thiazolinyl)-2-methoxy-imino-acetamido]-3-[(8-carboxymethyl-tetrazolo[1,5-b]pyridazin-6-yl)-thiomethyl]-3-cephem-4-carboxylic acid (syn isomer);

(29) 7β-[2-(2-imino-3-hydroxy-4-thiazolinyl)-2-methoxy-imino-acetamido]-3-[(2,3-dihydro-2-methyl-3-oxo-1,2,4-triazolo[4,3,b]pyridazin-6-yl)-thiomethyl]-3-cephem-4-carboxylic acid (syn isomer);

(30) 7β-[2-(2-imino-3-methoxy-4-thiazolinyl)-2-methoxy-imino-acetamido]-3-[(1-methyl-1,2,3,4-tetrazol-5-yl)-thiomethyl]-3-cephem-4-carboxylic acid (syn-isomer);

(31) 7β-[2-(2-imino-3-methoxy-4-thiazolinyl)-2-methoxy-imino-acetamido]-3-[(1-[2-propenyl]-1,2,3,4-tetrazol-5-yl)-thiomethyl]-3-cephem-4-carboxylic acid (syn-isomer);

(32) 7β-[2-(2-imino-3-methoxy-4-thiazolinyl)-2-methoxy-imino-acetamido]-3-[(1-[2-cyanoethyl]-1,2,3,4-tetrazol-5-yl)-thiomethyl]-3-cephem-4-carboxylic acid (syn-isomer);

(33) 7β-[2-(2-imino-3-methoxy-4-thiazolinyl)-2-methoxy-imino-acetamido]-3-[(5-methyl-1,3,4-thiadiazol-2-yl)-thiomethyl]-3-cephem-4-carboxylic acid (syn-isomer);

(34) 7β-[2-(2-imino-3-methoxy-4-thiazolinyl)-2-methoxy-imino-acetamido]-3-[(tetrazolo[1,5-b]pyridazin-6-yl)-thiomethyl]-3-cephem-4-carboxylic acid (syn-isomer);

(35) 7β-[2-(2-imino-3-methoxy-4-thiazolinyl)-2-methoxy-imino-acetamido]-3-[(8-amino-tetrazolo[1,5-b]pyridazin-6-yl)-thiomethyl]-3-cephem-4-carboxylic acid (syn-isomer);

(36) 7β-[2-(2-imino-3-methoxy-4-thiazolinyl)-2-methoxy-imino-acetamido]-3-[(8-carboxy-tetrazolo[1,5-b]pyridazin-6-yl)-thiomethyl]-3-cephem-4-carboxylic acid (syn-isomer);

(37) 7β-[2-(2-imino-3-methoxy-4-thiazolinyl)-2-methoxy-imino-acetamido]-3-[(8-carboxymethyl-tetrazolo[1,5-b]pyridazin-6-yl)-thiomethyl]-3-cephem-4-carboxylic acid (syn-isomer);

(38) 7β-[2-(2-imino-3-hydroxy-4-thiazolinyl)-2-carboxymethoxy-imino-acetamido]-3-[(1-methyl-1,2,3,4-tetrazol-5-yl)-thiomethyl]-3-cephem-4-carboxylic acid (syn isomer);

(39) 7β-[2-(2-imino-3-hydroxy-4-thiazolinyl)-2-carboxymethoxy-imino-acetamido]-3-[(5-methyl-1,3,4-thiadiazol-2-yl)-thiomethyl]-3-cephem-4-carboxylic acid (syn-isomer);

(40) 7β-[2-(2-imino-3-hydroxy-4-thiazolinyl)-2-carboxymethoxy-imino-acetamido]-3-[(8-amino-tetrazolo[1,5-b]pyridazin-6-yl)-thiomethyl]-3-cephem-4-carboxylic acid (syn isomer);

(41) 7β-[2-(2-imino-3-methoxy-4-thiazolinyl)-2-carboxymethoxy-imino-acetamido]-3-[(1-methyl-1,2,3,4-tetrazol-5-yl)-thiomethyl]-3-cephem-4-carboxylic acid (syn isomer);

(42) 7β-[2-(2-imino-3-methoxy-4-thiazolinyl)-2-carboxymethoxy-imino-acetamido]-3-[(5-methyl-1,3,4-thiadiazol-2-yl)-thiomethyl]-3-cephem-4-carboxylic acid (syn-isomer);

(43) 7β-[2-(2-imino-3-methoxy-4-thiazolinyl)-2-carboxymethoxy-imino-acetamido]-3-[(8-amino-tetrazolo[1,5-b]pyridazin-6-yl)-thiomethyl]-3-cephem-4-carboxylic acid (syn isomer);

(44) 7β-[2-(2-imino-3-hydroxy-4-thiazolinyl)-2-(β-carboxy-vinylene-oxy-imino)acetamido]-3-[(8-amino-tetrazolo[1,5-b]pyridazin-6-yl)-thiomethyl]-3-cephem-4-carboxylic acid (syn isomer);

(45) 7β-[2-(2-imino-3-amino-4-thiazolinyl)-2-methoxy-imino-acetamido]-3-[(1-methyl-1,2,3,4-tetrazol-5-yl)-thiomethyl]-3-cephem-4-carboxylic acid (syn isomer);

(46) 7β-[2-(2-imino-3-amino-4-thiazolinyl)-2-methoxy-imino-acetamido]-3-[(5-methyl-1,3,4-thiadiazol-2-yl)-thiomethyl]-3-cephem-4-carboxylic acid (syn isomer);

(47) 7β-[2-(2-imino-3-amino-4-thiazolinyl)-2-methoxy-imino-acetamido]-3-[(tetrazolo[1,5-b]pyridazin-6-yl)-thiomethyl]-3-cephem-4-carboxylic acid (syn isomer);

(48) 7β-[2-(2-imino-3-amino-4-thiazolinyl)-2-methoxy-imino-acetamido]-3-[(8-amino-tetrazolo[1,5-b]pyridazin-6-yl)-thiomethyl]-3-cephem-4-carboxylic acid (syn isomer);

(49) 7β-[2-(2-imino-3-amino-4-thiazolinyl)-2-carboxymethoxyimino-acetamido]-3-[(1-methyl-1,2,3,4-tetrazol-5-yl)-thiomethyl]-3-cephem-4-carboxylic acid (syn isomer);

(50) 7β-[2-(2-imino-3-amino-4-thiazolinyl)-2-(β-carboxyvinylene-oxy-iminoacetamido]-3-[(1-methyl-1,2,3,4-tetrazol-5-yl)-thiomethyl]-3-cephem-4-carboxylic acid (syn isomer);

(51) 7β-[2-(2-imino-3-hydroxy-4-thiazolinyl)-2-methoxyiminoacetamido]-1-sulphone-3-cephem-4-carboxylic acid (syn isomer);

(52) 7β-[2-(2-imino-3-hydroxy-4-thiazolinyl)-2-methoxyiminoacetamido]-1-sulphone-3-acetoxymethyl-3-cephem-4-carboxylic acid (syn isomer);

(53) 7β-[2-(2-imino-3-methoxy-4-thiazolinyl)-2-methoxyiminoacetamido]-1-sulphone-3-acetoxymethyl-3-cephem-4-carboxylic acid (syn isomer);

(54) 7β-[2-(2-imino-3-amino-4-thiazolinyl)-2-methoxyiminoacetamido]-1-sulphone-3-acetoxymethyl-3-cephem-4-carboxylic acid (syn isomer);

(55) 7β-[2-(2-imino-3-hydroxy-4-thiazolinyl)-2-(α-methyl-α-carboxyethoxy-imino)acetamido]-3-acetoxymethyl-3-cephem-4-carboxylic acid (syn isomer);

(56) 7β-[2-(2-imino-3-methoxy-4-thiazolinyl)-2-(α-methyl-α-carboxyethoxy-imino)acetamido]-3-acetoxymethyl-3-cephem-4-carboxylic acid (syn isomer);

(57) 7β-[2-(2-imino-3-amino-4-thiazolinyl)-2-(α-methyl-α-carboxyethoxy-imino)acetamido]-3-acetoxymethyl-3-cephem-4-carboxylic acid (syn isomer);

(58) 7β-[2-(2-imino-3-hydroxy-4-thiazolinyl)-2-methoxyiminoacetamido]-3-[8-aminocarbonyltetrazolo[1,5-b]pyridazin-6-yl-thiomethyl]-3-cephem-4-carboxylic acid (syn-isomer);

(59) 7β-[2-(2-imino-3-methoxy-4-thiazolinyl)-2-methoxyiminoacetamido]-3-[8-aminocarbonyltetrazolo[1,5-b]pyridazin-6-yl-thiomethyl]-3-cephem-4-carboxylic acid (syn-isomer);

(60) 7β-[2-(2-imino-3-amino-4-thiazolinyl)-2-methoxyiminoacetamido]-3-[8-aminocarbonyltetrazolo[1,5-b]pyridazin-6-yl-thiomethyl]-3-cephem-4-carboxylic acid (syn-isomer), and the pharmaceutically and veterinarily acceptable salts (e.g. the hydrochlorides) and esters thereof.

The structural formulae of the above-numbered compounds are shown in the following Table:

TABLE

| Compound | $R_1$ | R | $R_3$ | n | X | Y |
|---|---|---|---|---|---|---|
| 1 | —H | —OH | —H | zero | —COOH | —H |
| 2 | —H | —OH | —CH$_3$ | zero | —COOH | —H |
| 3 | —H | —OH | —CH$_3$ | 1(R) | —COOH | —H |
| 4 | —H | —OH | —CH$_3$ | 1(S) | —COOH | —H |
| 5 | —H | —OH | —CH$_3$ | zero | —COOH | —Cl |
| 6 | —H | —OH | —CH$_3$ | zero | —COOH | —OH |
| 7 | —H | —OH | —CH$_3$ | zero | —COOH | —OCH$_3$ |
| 8 | —H | —OCH$_3$ | —CH$_3$ | zero | —COOH | —H |
| 9 | —H | —NH$_2$ | —CH$_3$ | zero | —COOH | —H |

TABLE-continued

| Compound | R₁ | R | R₃ | n | X | Y |
|---|---|---|---|---|---|---|
| 10 | —H | —OH | —CH₃ | zero | —COOH | —CH₂OCOCH₃ |
| 11 | —H | —OH | —CH₃ | 1(R) | —COOH | —CH₂OCOCH₃ |
| 12 | —H | —OH | —CH₃ | 1(S) | —COOH | —CH₂OCOCH₃ |
| 13 | —H | —NH₂ | —CH₃ | zero | —COOH | —CH₂OCOCH₃ |
| 14 | —H | —NH₂ | —CH₃ | 1(R) | —COOH | —CH₂OCOCH₃ |
| 15 | —H | —NH₂ | —CH₃ | 1(S) | —COOH | —CH₂OCOCH₃ |
| 16 | —H | —OCH₃ | —CH₃ | zero | —COOH | —CH₂OCOCH₃ |
| 17 | —H | —OCH₃ | —CH₃ | 1(R) | —COOH | —CH₂OCOCH₃ |
| 18 | —H | —OCH₃ | —CH₃ | 1(S) | —COOH | —CH₂OCOCH₃ |
| 19 | —H | —OH | —CH₃ | zero | —COOH | —CH₂—S—(1-methyl-tetrazol-5-yl) |
| 20 | —H | —OH | —CH₃ | zero | —COOH | —CH₂—S—(1-allyl-tetrazol-5-yl) |
| 21 | —H | —OH | —CH₃ | zero | —COOH | —CH₂—S—(1-(2-cyanoethyl)-tetrazol-5-yl) |
| 22 | —H | —OH | —CH₃ | zero | —COOH | —CH₂—S—(5-methyl-1,3,4-thiadiazol-2-yl) |
| 23 | —H | —OH | —CH₃ | zero | —COOH | —CH₂—S—(5-methylthio-1,3,4-thiadiazol-2-yl) |
| 24 | —H | —OH | —CH₃ | zero | —COOH | —CH₂—S—(5-amino-1,3,4-thiadiazol-2-yl) |
| 25 | —H | —OH | —CH₃ | zero | —COOH | —CH₂—S—(tetrazolo[1,5-b]pyridazin-6-yl) |
| 26 | —H | —OH | —CH₃ | zero | —COOH | —CH₂—S—(8-amino-tetrazolo[1,5-b]pyridazin-6-yl) |
| 27 | —H | —OH | —CH₃ | zero | —COOH | —CH₂—S—(8-carboxy-tetrazolo[1,5-b]pyridazin-6-yl) |
| 28 | —H | —OH | —CH₃ | zero | —COOH | —CH₂—S—(8-carboxymethyl-tetrazolo[1,5-b]pyridazin-6-yl) |
| 29 | —H | —OH | —CH₃ | zero | —COOH | —CH₂—S—(2-methyl-3-oxo-2H-[1,2,4]triazolo[4,3-b]pyridazin-6-yl) |

TABLE-continued

| Compound | $R_1$ | R | $R_3$ | n | X | Y |
|---|---|---|---|---|---|---|
| 30 | —H | —OCH$_3$ | —CH$_3$ | zero | —COOH | —CH$_2$—S—C(=N—N=N—N(CH$_3$)—) (1-methyltetrazol-5-ylthiomethyl) |
| 31 | —H | —OCH$_3$ | —CH$_3$ | zero | —COOH | —CH$_2$—S—(1-allyltetrazol-5-yl), N-substituent = —CH$_2$—CH=CH$_2$ |
| 32 | —H | —OCH$_3$ | —CH$_3$ | zero | —COOH | —CH$_2$—S—(1-(2-cyanoethyl)tetrazol-5-yl), N-substituent = —CH$_2$CH$_2$CN |
| 33 | —H | —OCH$_3$ | —CH$_3$ | zero | —COOH | —CH$_2$—S—(5-methyl-1,3,4-thiadiazol-2-yl) |
| 34 | —H | —OCH$_3$ | —CH$_3$ | zero | —COOH | —CH$_2$—S—(tetrazolo[1,5-b]pyridazin-6-yl) |
| 35 | —H | —OCH$_3$ | —CH$_3$ | zero | —COOH | —CH$_2$—S—(8-amino-tetrazolo[1,5-b]pyridazin-6-yl) |
| 36 | —H | —OCH$_3$ | —CH$_3$ | zero | —COOH | —CH$_2$—S—(8-carboxy-tetrazolo[1,5-b]pyridazin-6-yl) |
| 37 | —H | —OCH$_3$ | —CH$_3$ | zero | —COOH | —CH$_2$—S—(8-carboxymethyl-tetrazolo[1,5-b]pyridazin-6-yl) |
| 38 | —H | —OH | —CH$_2$COOH | zero | —COOH | —CH$_2$—S—(1-methyltetrazol-5-yl) |
| 39 | —H | —OH | —CH$_2$COOH | zero | —COOH | —CH$_2$—S—(5-methyl-1,3,4-thiadiazol-2-yl) |
| 40 | —H | —OH | —CH$_2$COOH | zero | —COOH | —CH$_2$—S—(8-amino-tetrazolo[1,5-b]pyridazin-6-yl) |
| 41 | —H | —OCH$_3$ | —CH$_2$COOH | zero | —COOH | —CH$_2$—S—(1-methyltetrazol-5-yl) |
| 42 | —H | —OCH$_3$ | —CH$_2$COOH | zero | —COOH | —CH$_2$—S—(5-methyl-1,3,4-thiadiazol-2-yl) |

TABLE-continued

| Compound | R₁ | R | R₃ | n | X | Y |
|---|---|---|---|---|---|---|
| 43 | —H | —OCH₃ | —CH₂COOH | zero | —COOH | —CH₂—S—[6-amino-pyridazino-tetrazole] |
| 44 | —H | —OH | —CH=CH—COOH | zero | —COOH | —CH₂—S—[6-amino-pyridazino-tetrazole] |
| 45 | —H | —NH₂ | —CH₃ | zero | —COOH | —CH₂—S—[1-methyl-tetrazol-5-yl] |
| 46 | —H | —NH₂ | —CH₃ | zero | —COOH | —CH₂—S—[5-methyl-1,3,4-thiadiazol-2-yl] |
| 47 | —H | —NH₂ | —CH₃ | zero | —COOH | —CH₂—S—[pyridazino-tetrazole] |
| 48 | —H | —NH₂ | —CH₃ | zero | —COOH | —CH₂—S—[amino-pyridazino-tetrazole] |
| 49 | —H | —NH₂ | —CH₂COOH | zero | —COOH | —CH₂—S—[1-methyl-tetrazol-5-yl] |
| 50 | —H | —NH₂ | —CH=CH—COOH | zero | —COOH | —CH₂—S—[1-methyl-tetrazol-5-yl] |
| 51 | —H | —OH | —CH₃ | 2 | —COOH | —H |
| 52 | —H | —OH | —CH₃ | 2 | —COOH | —CH₂OCOCH₃ |
| 53 | —H | —OCH₃ | —CH₃ | 2 | —COOH | —CH₂OCOCH₃ |
| 54 | —H | —NH₂ | —CH₃ | 2 | —COOH | —CH₂OCOCH₃ |
| 55 | —H | —OH | —C(CH₃)₂—COOH | zero | —COOH | —CH₂OCOCH₃ |
| 56 | —H | —OCH₃ | —C(CH₃)₂—COOH | zero | —COOH | —CH₂OCOCH₃ |
| 57 | —H | —NH₂ | —C(CH₃)₂—COOH | zero | —COOH | —CH₂OCOCH₃ |
| 58 | —H | —OH | —CH₃ | zero | —COOH | —CH₂—S—[4-carbamoyl-pyridazino-tetrazole] |

TABLE-continued

| Compound | R₁ | R | R₃ | n | X | Y |
|---|---|---|---|---|---|---|
| 59 | —H | —OCH₃ | —CH₃ | zero | —COOH | ![structure with —CH₂—S— linked pyridazine-triazole bearing CONH₂] |
| 60 | —H | —NH₂ | —CH₃ | zero | —COOH | ![structure with —CH₂—S— linked pyridazine-triazole bearing CONH₂] |

The compounds of the invention can be prepared by a process comprising:

(a) reacting a compound of formula (II)

$$\text{(II)}$$

wherein
n, X and Y are as defined above and E is amino, —N=C=O or —N=C=S or a reactive derivative thereof, with a compound of formula (III)

$$\text{(III)}$$

wherein
R is as defined above and R₁ and R₃ have the meanings defined above except hydrogen, or a reactive derivative thereof, and, if desired, removing the protecting groups, where present; or (b) reacting a compound of formula (IV)

$$\text{(IV)}$$

wherein
R₃, n, X and Y are as defined above, or a reactive derivative thereof, with a compound of formula (V)

$$R-NH_2 \quad \text{(V)}$$

wherein R is as defined above, or a salt thereof and, if desired, removing the protecting groups possibly present in R₃ and/or in R₆, thus giving a compound of formula (I) where R₁ is hydrogen; or (c) reacting a compound of formula (VI)

$$\text{(VI)}$$

wherein
R, R₁, n, X and Y are as defined above, with a nitrosating agent, and, if desired, removing the protecting groups possibly present in R and R₁, thus giving a compound of formula (I) wherein R₃ is hydrogen; or (d) reacting a compound of formula (VII)

$$\text{(VII)}$$

wherein
R, R₁, n, X and Y are as defined above, with a compound of formula (VIII)

$$H_2N-OR_3 \quad \text{(VIII)}$$

wherein
R₃ is as defined above and, if desired, removing the protecting groups where present; or (e) reacting a compound of formula (IX)

$$\text{(IX)}$$

wherein $R_3$, n, X and Y are as defined above and B is halogen, with a compound of formula (X)

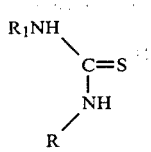

wherein
R and $R_1$ are as defined above and, if desired, removing the protecting groups, where present; or (f) reacting a compound of formula (XI)

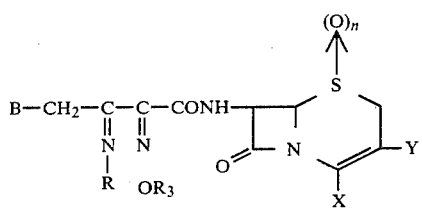

wherein B, R, $R_3$, n, X and Y are as defined above with thiocyanic acid, or a salt thereof, and, if desired, removing the protecting groups, where present, thus giving a compound of formula (I) where $R_1$ is hydrogen; or (g) reacting a compound of formula (XII)

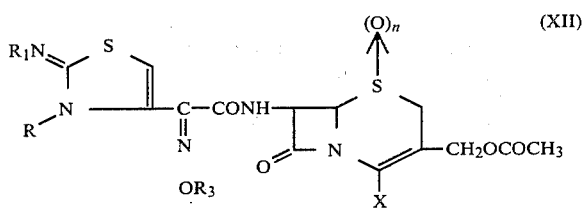

wherein R, $R_1$, $R_3$, n and X are as defined above, or a reactive derivative thereof, with a compound of formula (XIII)

HS—Het     (XIII)

wherein Het is as defined above, or a reactive derivative thereof, and, if desired, removing the protecting groups, where present; or (h) reacting a compound of formula (I) wherein R is hydrogen and $R_1$, $R_3$, n, X and Y are as defined above with an oxidizing agent and, if desired, removing the protecting groups, where present, thus giving a compound of formula (I) wherein R is hydroxy and n is 2, and, if desired, converting a compound of formula (I) where X is a free carboxy group into a pharmaceutically or veterinarily acceptable salt and/or, if desired, obtaining a free compound from a salt and/or, if desired, resolving a mixture of isomers into the single isomers and/or, if desired, converting a compound of formula (I) or a salt thereof into another compound of formula (I) or a salt thereof.

When in the compound having the formulae (II), (IV), (VI), (VII), (IX), (XI) and (XII) X is a free carboxy group, the carboxy group may be protected, if necessary, in a conventional manner before the reaction takes place.

Examples of protecting groups are those usually employed in the synthesis of peptides, for example, tert-butyl, benzhydryl, p-methoxybenzyl, p-nitrobenzyl, trityl and trialkylsilyl.

The protecting groups are then removed, at the end of the reaction, in a known manner, e.g. by mild acid hydrolysis or by catalytic hydrogenation, for example, with Pd/C at room pressure.

Since, however, compounds of formula (I) containing the said protecting groups are included in the present invention, removal of the protecting groups is not an essential process step.

The starting materials used in each of the above-mentioned processes (a) to (h), when one or more asymmetric carbon atoms are present, may be either optically active or racemic compounds.

Furthermore, the starting material may be syn- or anti-isomers and their mixtures, as well as cis- or trans-isomers and their mixtures.

A reactive derivative of the compound of formula (II) may be, for example, an amine salt, a silyl ester or a metal salt when X is carboxy.

A reactive derivative of the compound of formula (III) may be, for example, an acyl halide, an anhydride or a mixed anhydride, an amide, an azide, a reactive ester or a salt, such as, for instance, the salts formed with alkaline or alkaline-earth metals, ammonia or an organic basis.

A reactive ester may be, for example, p-nitrophenyl ester; 2,4-dinitrophenyl ester, pentachlorophenyl ester, N-hydroxysuccinimide ester and N-hydroxyphthalimide ester.

A reactive derivative of a compound of formula (IV) may be, for instance, a salt or an ester of a compound (IV) where X is —COOH. The reaction between the compound of formula (II) or a reactive derivative thereof and the compound of formula (III) or a reactive derivative thereof may be performed either at room temperature or under cooling, preferably from about $-50°$ C. to about $+40°$ C. in a suitable solvent, e.g. acetone, dioxane, tetrahydrofuran, acetonitrile, chloroform, methylene chloride, dimethylformamide 1,2-dichloroethane or in a mixture of water and a solvent miscible with water and, if necessary, in the presence of a base, for example sodium bicarbonate, potassium bicarbonate or a trialkylamine, or in the presence of another acid acceptor, such as an alkylene oxide, e.g. propylene oxide.

When the compound of formula (III) is reacted with the compound of formula (II) wherein E is amino, as a free acid or as a salt, it is desirable that the reaction be performed in the presence of a condensing agent, such as, for example, N,N'-dicyclohexylcarbodiimide. The optional removal of the protecting groups, at the end of the reaction, may be performed in a known manner. For example, the tert-butoxycarbonyl group may be removed by treatment with a solution of an acid (for example $CF_3COOH$ or HCOOH) and the monochloroacetyl group may be removed by treatment with thiourea. The formyl and the trifluoroacetyl groups may be removed by treatment with potassium carbonate in aqueous methanol; the tetrahydropyranyl group by treatment with dilute hydrochloric acid and the trityl group by treatment with formic or trifluoracetic acid. The reaction between the compound of formula (IV) or a salt or an ester thereof with a compound of formula (V) or a salt thereof may be performed in a suitable solvent, e.g. water, methanol, ethanol, dioxane, acetonitrile, dimethylformamide, dimethylacetamide, methylene chloride.

A salt of the compound of formula (V) may be a salt with an inorganic acid, e.g. hydrochloric acid or sulphuric acid, or with an organic acid, e.g. citric, tartaric, oxalic or, p-toluenesuphonic acid.

The reaction temperature preferably ranges from about 0° C. to about 90° C. and the pH is preferably maintained from about 1 to about 7.5. The subsequent optional removal of the protecting groups may be performed by known methods e.g. those indicated above.

The nitrosation of the compound of formula (VI) may be performed using as nitrosating agent nitrosyl chloride or an organic or inorganic nitrite, for instance amyl nitrite, sodium nitrite or potassium nitrite in the presence of an acid, for instance hydrochloric acid or acetic acid. The nitrosation reaction may be performed at room temperature or under cooling, the preferred temperature range being from about $-20°$ C. to about $40°$ C., in a suitable solvent, e.g. dioxane, acetonitrile, tetrahydrofuran, acetic acid or a mixture of one of these solvents with water.

Before the nitrosation, the carboxy groups present may be, if necessary, salified, e.g., by treatment with an alkali metal hydroxide or protected e.g. by one of the protecting groups mentioned above. The protecting groups may be removed by known methods at the end of the reaction, e.g. as indicated above.

The reaction between the compound of formula (VII), or a salt or an ester thereof, with the compound of formula (VIII) is preferably carried out in water or in a polar solvent, such as methanol, ethanol, acetone, dioxane, tetrahydrofuran, acetonitrile, dimethylformamide or in a mixture of water and one of the above mentioned solvents at a pH ranging from about 1 to about 7.5, preferably from 4 to 5, and at temperatures from about $-20°$ C. to about $+50°$ C., preferably between $+5°$ C. and room temperature.

The reaction between the compound of formula (IX), or a salt or an ester thereof, and the compound of formula (X) is preferably carried out in an aprotic solvent e.g. N,N-dimethylformamide, N,N-dimethylacetamide, dimethylsulphoxide, acetonitrile, hexamethylphosphorotriamide, or in a mixture of these solvents. The reaction temperature preferably ranges from about 0° C. to about 90° C. The subsequent optional removal of the protecting groups possibly present, may be carried out as indicated above.

The reaction between a compound of formula (XI) with thiocyanic acid or a salt thereof, e.g. potassium thiocyanate, may be performed in an inert solvent preferably a dipolar aprotic solvent, like acetonitrile or dimethylacetamide.

The reaction between the compound of formula (XII) or a salt thereof and the compound of formula (XIII), or a reactive derivative thereof, for example an alkaline salt, may be carried out in water or in a mixture of water and an organic solvent e.g. acetone, ethanol, dioxane or tetrahydrofuran, in the presence of about 2 equivalents of a base, for example sodium bicarbonate. The reaction temperature preferably ranges from about 5° C. to about 90° C. and the pH is preferably maintained from about 5 to about 7.5. If desired, a buffer may be used, for example sodium phosphate or acetate. In a different way, the same reaction may be performed without any base and in a strictly anhydrous solvent, at temperatures ranging from about 50° C. to about 120° C., and for reaction times ranging from a few hours to a few days.

The preferred solvent is acetonitrile and an inert atmosphere (e.g. nitrogen) may be advisable in order to prevent the oxidation of the heterocyclic thiol (XIII).

The subsequent optional removal of the protecting groups may be performed by known methods e.g. those indicated above.

The oxidation of the compound of formula (I) wherein R is hydrogen to obtain a compound (I) where R is hydroxy and n is 2 may be performed by the same oxidizing agents used to obtain sulphones from sulphides that is e,g., a peracid, for example, perbenzoic, m-chloroperbenzoic or permaleic acid, sodium periodate, hydrogen peroxide or a mixture of one of these with an inorganic or organic acid, e.g., formic acetic or trifluoro acetic acid. The reaction may be performed in a solvent, dioxane, tetrahydrofuran, chloroform, methylene chloride, formic acid, acetic acid, benzene, dimethylformamide, dimethylacetamide or the like at a temperature ranging from about $-30°$ C. to about $+90°$ C. During this reaction $R_1$ must be an amine-protecting group, e.g. one of the protecting groups indicated above, which may be then removed by known methods at the end of the reaction.

The optional salification of the compound of formula (I) as well as the optional conversion of a salt into a free compound, may be carried out according to conventional methods, i.e. methods already known in organic chemistry.

As stated above, a compound of formula (I) or a salt thereof, may be converted into another compound of formula (I) or a salt thereof; also these optional conversions may be performed by conventional methods. Thus, for example a compound of formula (I) wherein $R_2$ or $R_3$ is other than hydrogen may be obtained starting from the corresponding compounds wherein $R_2$ or $R_3$ is hydrogen by the usual etherification or esterification reactions described in the organic chemistry. Other optional conversions may be also the esterification of a compound of formula (I), wherein X is carboxy, which may be carried out by reacting the compound of formula (I), wherein the carboxy group is free or salified, for example in the form of a sodium, potassium, calcium or triethylammonium salt, with the suitable halide, in an organic solvent, e.g. acetone, tetrahydrofuran, chloroform, methylene chloride, dimethylformamide, dimethylsulphoxide, or in a mixture of water and an organic solvent, e.g. dioxane and acetone; the reaction temperatures range from about $-20°$ C. to about $+80°$ C.

Furthermore a compound of formula (I), wherein X is an esterified carboxy group, may be saponified using, for example, an inorganic acid, e.g. hydrochloric acid or trifluoroacetic acid, as known in organic chemistry.

Also the optional resolution of a mixture of isomers into the single isomers may be carried out by conventional methods. Thus, racemic compounds may be resolved into the optical antipodes, for example, by resolution, e.g. by means of fractional crystallization of mixtures of diastereoisomeric salts, and, if desired, liberating the optical antipodes from the salts.

The compounds of formula (I) wherein n is 1 and wherein the sulphoxide is in the S configuration, may be preferably obtained from the corresponding compounds of formula (I) wherein n is zero by treatment with an oxidizing agent especially a peracid, for example perbenzoic acid, m-chloroperbenzoic acid, permaleic acid, sodium periodate, hydrogen peroxide or a mixture of these, with an inorganic or organic acid e.g. formic acid, acetic acid or trifluoroacetic acid.

The reaction may be performed in a solvent, e.g., dioxane, tetrahydrofuran, chloroform, methylene chloride, formic acid, acetic acid, benzene, N,N-dimethylformamide, N,N-dimethylacetamide or the like. The reaction temperature is preferably from about −30° C. to about +90° C.

To obtain the sulphoxide with the R-configuration it is preferable to carry out the same oxidation reaction on the intermediate products, preferably on the compounds of formula (II) wherein E is amino, after first protecting this amino group by formation of a Schiff base.

The Schiff base may be prepared by known methods e.g. by treatment of the amine of formula (II) with an aldehyde such as benzaldehyde, salicylaldehyde or p-nitrobenzaldehyde; at the end of the oxidation reaction the free amino group may be obtained for example by treatment with a hydrazine derivative, for instance phenylhydrazine, 2,4-dinitrophenylhydrazine or a Girard reagent. The carboxy group is preferably protected during the oxidation reaction using e.g., as protecting groups those mentioned above.

The conversion of sulphide to sulphoxide, e.g. the conversion of a compound of formula (I) wherein n is zero into the corresponding compound wherein n is 1, may be effected by using 1-1.2 molar equivalents of the oxidizing agent for each mole of the compound to be oxidized.

The conversion sulphide to sulphone, i.e. the conversion of a compound of formula (I) wherein n is zero into the corresponding compound of formula (I) wherein n is 2, may be performed by the same oxidizing agents used to obtain the sulphoxides, using in this case at least two molar equivalents of the oxidizing agent for each mole of the compound to be oxidized.

The compound of formula (II), wherein E is amino, and Y is —CH$_2$—S—Het may be prepared, for example, by reacting 7-amino-cephalosporanic acid or a salt thereof with the compound of formula (XIII), using reaction conditions well known in literature.

The compound of formula (II) wherein E is amino and Y is hydrogen, halogen, hydroxy, alkyl or alkoxy are known compounds or may be prepared by known methods.

The compounds of formula (II), wherein E is —N=C=O or —N=C=S may be prepared e.g. by reacting a compound of formula (II), wherein E is amino, with phosgene or thiophosgene, in the presence of a hydrochloric acid acceptor, using known methods.

The compound of formula (III) may be prepared according to one of the following methods:
(1) by treatment of a compound of formula (XIV)

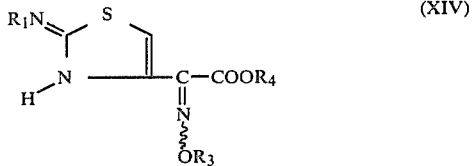

(XIV)

wherein $R_1$, $R_3$ and $R_4$ are as defined above, with an oxidizing agent especially a peracid, for example perbenzoic acid, m-chloroperbenzoic acid, permaleic acid, pertrifluoroacetic acid, sodium periodate, hydrogen peroxide or a mixture of these with an inorganic or organic acid, e.g. formic acid, acetic acid or trifluoroacetic acid, thus giving a compound of formula (III) wherein R is —OH. The reaction may be performed in a solvent, e.g. dioxane, methylene chloride, chloroform, methanol.

The reaction temperature is preferably from about −30° C. to about +90° C.

The compounds of formula (XIV) are known in literature, or may be prepared by known methods;
(2) by treatment of a compound of formula (XIV) with a N-aminating agent, such as, in particular, O-mesitylene sulfonyl hydroxylamine, thus giving the amonium mesitylene sulfonate salt of the compound of formula (III) wherein R is —NH$_2$, from which the free base can be obtained in a conventional manner. The reaction may be performed in an inert solvent e.g. chloroform, methylene chloride, at temperature ranging from −30° C. to +40° C.

(3) by reaction of a compound of formula (XV)

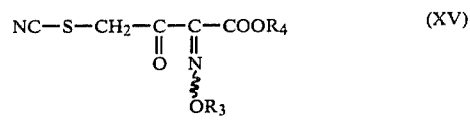

(XV)

wherein $R_3$ and $R_4$ are as defined above, with a compound of formula (V) using reaction conditions analogous to those indicated for the reaction between the compound of formula (IV) and the compound of formula (V).

The compound of formula (XV) are known compounds or may be prepared by known methods.
(4) by nitrosation of a compound of formula (XVI)

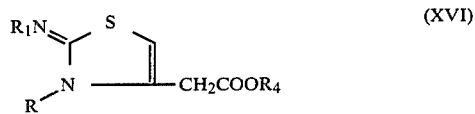

(XVI)

wherein R, $R_1$ and $R_4$ are as defined above, using reaction conditions analogous to those indicated for the nitrosation of compound of formula (VI).

The compounds of formula (XVI) may be prepared by reaction of a compound of formula (XVII)

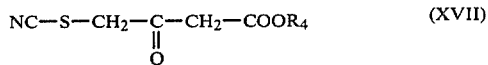

(XVII)

wherein $R_4$ is as defined above, using reaction conditions analogous to those indicated for the reaction between the compound of formula (IV) and the compound of formula (V).

The compounds of formula (XVI) wherein R is —OH or —NH$_2$ may be also prepared from a compound of formula (XVI) wherein R is hydrogen, using reaction conditions analogous to those described here above respectively in methods (1) and (2).

The compounds of formula (XVII) are known compounds or may be prepared by known methods.
(5) by reaction of a compound of formula (XVIII)

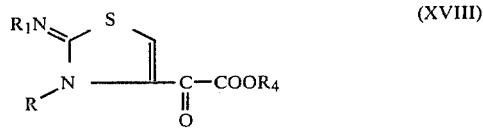

(XVIII)

wherein R, R₁ and R₄ are as defined above, with a compound of formula (VIII) using reaction conditions analogous to those described above for the reaction between the compound of formula (VII) and the compound of formula (VIII).

The compound of formula (XVIII) wherein R is —OH or —NH₂ may be prepared from a compound of formula (XVIII) wherein R is hydrogen, using reaction conditions analogous to those described here above respectively in methods (1) and (2).

The compounds of formula (XVIII) wherein R represents an hydrogen atom are known or may be prepared by known methods.

The compound of formula (IV) may be prepared from a compound of formula (IX) by reaction with thiocyanic acid or a salt thereof, e.g., potassium thiocyanate, in an inert solvent, preferably a dipolar aprotic solvent, like acetonitrile or dimethylacetamide.

The compounds of formula (V) are known or may be prepared by know methods.

The compound of formula (VI) may be prepared by reacting a compound of formula (XVI) wherein R and R₁ are as defined above and R₄ is hydrogen atom with a compound of formula (II) using reaction conditions analogous to those described above for the reaction between the compound of formula (II) and the compound of formula (III).

The compound of formula (VI) may also be prepared either by reacting a compound of formula (XIX)

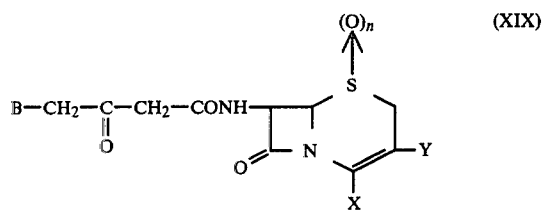

wherein B, n, X and Y are as defined above, with a compound of formula (X), using the same conditions reported in the method (e) above mentioned; or by reaction of a compound of formula (XX)

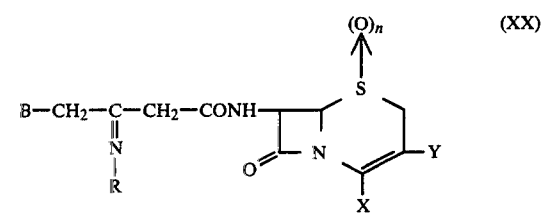

wherein B, R, n, X and Y are as defined above, with thiocyanic acid, or a salt thereof, using the same conditions reported in the method (f) above mentioned.

The compounds of formula (VII) may be prepared by reacting a compound of formula (XVIII) wherein R, R₁ are as defined above and R₄ is hydrogen atom, with a compound of formula (II), using reaction conditions analogous to those described above for the reaction between the compound of formula (II) and the compound of formula (III).

A compound of formula (VII) wherein R is hydroxy and n is 2 may also be prepared starting from a compound of formula (VII) wherein R is hydrogen, by reaction with an oxidizing agent, by the same procedure reported above for the analogous conversion of a compound of formula (I) where R is hydrogen into a compound of formula (I) where R is hydroxy and n is 2.

The compounds of formula (VIII), (IX) and (X) are known compounds or may be prepared by known methods.

The compounds of formula (XI) may be prepared starting from a compound of formula (IX) by reaction with a compound of formula H₂N-R wherein R is as defined above using reaction conditions analogous to those described above for the reaction between the compound of formula (VII) and a compound of formula (VIII).

The compounds of formula (XII) wherein n is zero may be prepared for example, by reacting 7-aminocephalosporanic acid or a salt thereof with a compound of formula (III) or a reactive derivative thereof using reaction conditions analogous to those described above for the reaction between the compound of formula (II) and the compound of formula (III).

The compounds of formula (XIII) are known compounds or may be prepared by known methods.

The compound having the formulae (II), (IV), (VI), (VII), (IX), (XI) and (XII) wherein n is 1 or 2, may be obtained by oxidizing the corresponding compounds wherein n is zero as described above for the analogous conversions on the compounds of formula (I). When the starting materials of formula (III), (IV), (IX), (XI) and (XII) are syn-isomers, the reaction products are syn-isomers too and vice versa. In some cases a little amount of the antiisomer might be obtained together with the syn-isomer. The separation of the isomers may be performed by known methods, e.g., by fractional crystallisation or by chromatography.

The compounds of the present invention have a high antibacterial activity both in animals and in humans against gram-positive and gram-negative bacteria normally susceptible to cephalosporins such as staphylococci, steptococci, diplococci, Klebsiella, *Escherichia coli, Proteus mirabilis,* Salmonella, Shigella, Haemophilus and Neisseria. The compounds of the invention show also a high activity against the strong beta-lactamase producer microorganisms, such as, for example, *Klebsiella aerogenes* 1082 E, *Escherichia coli Tem, Enterobacter cloacae* P99, and indole-positive Proteus and the like, as well as against *Pseudomonas aeruginosa* strains, which are normally resistant to most cephalosporins.

The activity of the compounds of the invention both against bacteria normally susceptible to cephalosporins and against beta-lactamase producers is higher than that of Cefazolin and Cefuroxime.

For example, compound 7β-[2-(2-imino-3-hydroxy-4-thiazolinyl)-2-methoxyimino-acetamido]-3-[(tetrazolo[1,5-b]pyridazin-6-yl)-thiomethyl]-3-cephem-4-carboxylic acid (syn-isomer) (designated as FCE 20635) is about 4 times more active than Cefazolin against streptococci and about 30 times more active than Cefazolin and about 40 times more active than Cefuroxime against most Gram-negative bacteria.

Against *Enterobacter aerogenes* ATCC 8308, *Enterobacter cloacae* 1321 E, *Salmonella typhi Watson* and *Shigella sonnei* ATCC 11060, compound FCE 20635 is from 15 to 60 times more active than Cefazolin and from 60 to 100 times more active than Cefuroxime.

Besides, compound FCE 20635 is at least from 100 to 600 times more active than Cefazolin and Cefuroxime against *Proteus vulgaris*×20, *Proteus mirabilis* ATCC 9921 and *Haemophilus influenzae*.

Another important property of compound FCE 20635 is its high activity against most beta-lactamase producers organisms, such as *Klebsiella aerogenes* 1082 E, *Enterobacter cloacae* P 99, *Escherichia coli* Tem. Against these microorganisms, compound FCE 20635 is from 100 to at least 1000 times more active than Cefazolin and Cefuroxime. Besides, FCE 20635 is from 30 to 60 times more active than HR-756 (Cefotaxime) against *Klebsiella aerogenes* 1082 E and *Enterobacter cloacae* P 99. Compound FCE 20635 is also more active than HR-756 against clinical isolates of indole-positive Proteus. Compound FCE 20635 is at least as active as Cefotaxime against *Bacteroides fragilis* VPI 9032.

Compound FCE 20635 showed a high activity in vivo tests; for example, in mice infected with *Escherichia coli* G, *Klebsiella pneumoniae* ATCC 10031, *Proteus mirabilis* ATCC 9921, *Escherichia coli* Tem., *Haemophilus influenzae*, *Salmonella typhi* Watson and *Proteus vulgaris* ×20, the compound is from 10 to 1800 times more active than Cefazolin.

The toxicity of the compounds of the invention is quite negligible and therefore they can be safely used in therapy. For example, the approximate acute toxicity ($LD_{50}$) of compound FCE 20635 in the mouse determined with single intravenous administrations of increasing doses and measured on the seventh day of treatment is greater than 2000 mg/kg.

Analogous activity and toxicity data have been found for the other compounds of the invention.

Owing to their high antibacterial activity either in animals or in humans against both Gram-positive and Gram-negative bacteria the compounds of the present invention are useful in the treatment of the infections caused by said microorganisms, such as, respiratory tract infections, for example, bronchitis, bronchopneumonia, pleurisy; hepatobiliary and abdominal infections, for example, septicemia; urinary tract infections, for example, pyelonephritis, cystitis; obstetrical and gynecological infections, for instance, cevicitis, endometritis; ear, nose and throat infections, for instance, otitis, sinusitis, parotitis.

The compounds of the invention may be administered, either to humans or to animals, in a variety of dosage forms, e.g., orally in the form of tablets, capsules, drops or syrups; rectally in the form of suppositories; parenterally, e.g., intravenously or intramuscolarly (as solutions or suspensions), with intravenous administration being preferred in emergency situation; by inhalation in the form of aerosols or solutions for nebulizers; intravaginally in the form, e.g. of bougies; or topically in the form of lotions, creams and ointments. The pharmaceutical or veterinary compositions containing the compounds of the invention may be prepared in a conventional way by employing the conventional carriers or diluents used for the other cephalosporins.

Conventional carriers or diluents are, for example, water, gelatine, lactose, starches, magnesium stearate, talc, vegetable oils, cellulose and the like. Daily doses in the range of about 1 to about 100 mg per kg of body weight may be used, in various animal species, the exact dose depending on the age, weight and condition of the subject to be treated and on the frequency and route of administration. A preferred way of administration of the compounds of the invention is the parenteral one: in this case the compounds may be administered, for example to adult humans, in an amount ranging from about 100 mg to about 200 mg pro dose, preferably about 150 mg pro dose, 1-4 times a day, dissolved in a suitable solvent, such as, for example sterile water or lidocaine hydrochloride solution for intramuscular injections, and sterile water, physiological saline solution, dextrose solution or the conventional intravenous fluids or electrolytes, for intravenous injections. Furthermore, the compounds of the invention may be used as antibacterial agents in a prophylactic manner, e.g., in cleaning or as surface disinfecting compositions, for example, at a concentration of about 0.2 to 1% by weight of such compounds admixed with suspended or dissolved in conventional inert dry or aqueous carriers for application by washing or spraying.

They are also useful as nutritional supplements in animal feeds.

Assessment of melting points was somewhat difficult in some cases, as the compounds tend to retain the solvent. In these cases, after the indication of the melting point, the word "dec." (decomposition) was added.

The I.R. spectra were determined in a solid phase on a Perkin-Elmer 125 spectrophotometer.

N.M.R. spectra were determined with a Bruker HX-90 (90 MHz) for the final compounds and with a Perkin-Elmer R-24B (60 MHz) for the intermedia tes in DMSO (dimethylsulphoxide) or $CDCl_3$, with $(CH_3)_4Si$ as internal standard; owing to the insolubility of a few compounds other solvents, such as d-trifluoroacetic acid or $d_5$-pyridine, were used when required.

The following examples illustrate but do not limit the present invention.

Preparation 1

2-[2-(N-chloroacetyl)-imino-3-hydroxy-4-thiazolinyl]-2-methoxyimino acetic acid (syn-isomer)

To a suspension of 2-[2-(N-chloroacetyl)-amino-4-thiazolyl]-2-methoxyimino acetic acid (5.8 g) in acetonitrile (100 ml) a solution of diphenyldiazomethane (4.24 g) in acetonitrile was added dropwise, under cooling at 0° C. After stirring for 30 minutes at room temperature, the solution was evaporated to dryness under vacuum. The residue was taken up with ethyl acetate, the solution was washed with aqueous sodium bicarbonate, dried and evaporated, thus giving 9.3 g (100%) of the benzhydryl ester, as a white foam.

NMR ($CDCl_3$): 3.98 (3H,s, =$NOCH_3$), 4.2 (2H,s, —$COCH_2Cl$), 6.9 (1H,s, —C$\underline{H}$ $Ph_2$), 7.1 (1H,s, 5-H on thiazoline ring), 7.3 (10H,s, —$Ph_2$).

A solution of 85% m-chloroperbenzoic acid (3.1 g) in chloroform (60 ml) was added to a solution of the above-prepared ester (4.65 g) in chloroform (40 ml), under cooling at 0° C.

After stirring for 12 hours at room temperature, the solution was evaporated to dryness under vacuum. The residue was taken up with hot benzene (20 ml), then cooled, m-chlorobenzoic acid crystallized and was filtered off. The filtrate was evaporated to dryness under vacuum; ethyl ether (30 ml) was added to the residual gel and the mixture was gently heated. Soon after the complete dissolution the benzhydryl ester of the title compound starts crystallizing from the ethereal mother liquors.

After cooling 1 hour at 0° C., the crystals were collected, washed with ether and dried, thus affording 3.85 g (80%) of the benzhydryl ester of 2-[2-(N-chloroacetyl)-imino-3-hydroxy-4-thiazolinyl]-2-methoxyimino acetic acid, slightly contaminated (~2–5%) by the starting material. Pure product can be obtained by crystallizing from methanol; m.p.=164°–165° C.

Elemental Analysis: Found: C 55.06; H 4.01; N 9.16; Cl 7.72; S 6.60: Calculated for $C_{21}H_{18}ClN_3O_5S$: C 54.84; H 3.94; N 9.13; Cl 7.70; S 6.97.

NMR (CDCl$_3$): 3.97 (2H, s, —COCH$_2$Cl), 4.07 (3H, s, =NOCH$_3$), 7–7.4 (12H, m, —CHPh$_2$ and 5-H on thiazoline ring), 8.7 (1H, br-s, —OH).

NMR (DMSO-d$_6$): 4.05 (3H, s, =NOCH$_3$), 4.55 (2H, s, —COCH$_2$Cl), 6.99 (1H, s, —CHPh$_2$), 7.4 (1OH, s, Ph$_2$), 7.73 (1H, s, 5-H on thiazoline ring).

A solution of this ester (4.59 g) in TFA (45 ml) was stirred for 4 hours at room temperature, and then evaporated to dryness under vacuum. The residue was taken up with ethyl acetate and evaporated again to dryness.

The residue was triturated with ethyl ether, the precipitate produced was collected, suspended in chloroform, stirred for 15 minutes at room temperature and filtered. This treatment was repeated twice, in order to remove a little amount of the starting material. The solid was then washed with ethyl ether and crystallized from methanol, thus giving 2.43 g (82,5%) of 2-[2-(N-chloroacetyl)-imino-3-hydroxy-4-thiazolinyl]-2-methoxyimino acetic acid m.p.=157° dec.

Elemental Analysis: Found: C 32.77; H 2.81; N 14.29; S 10.85: Calculated for $C_8H_8ClN_3O_5S$: C 32.71; H 2.74; N 14.31; S 10.91.

NMR (DMSO-d$_6$): 3.98 (3H, s,=NOCH$_3$), 4.5 (2H, s,

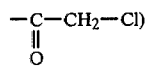

7.0 (2H, br-s, —OH and —COOH) 7.5 (1H, s, 5-H on thiazoline ring).

Preparation 2

2-(2-imino-3-hydroxy-4-thiazolinyl)-2-methoxyimino acetic acid (syn-isomer).

A solution of 2[2-(N-chloroacetyl)-imino-3-hydroxy-4-thiazolinyl]-2-methoxyimino acetic acid (2.93 g) and thiourea (0.76 g) in N,N-dimethylacetamide (10 ml) was stirred for 2 hours at room temperature. Ethyl ether was then added giving an oily product; the supernatant mother liquors were discarded and the residue was triturated with ethyl acetate until a powder was obtained.

The solid material was filtered, treated again with fresh ethyl ether, thus giving a mixture of the title product and pseudothiohydantoin (aprox. 3.5 g; almost quantitative yield) partially as HCl salts.

Crystallization from water of this mixture then afforded the pure title compound (as internal salt) m.p.=209°–210° C.

Elemental Analysis: Found: C 32.98; H 3.18; N 19.15; S 14.63: Calculated for $C_6H_7N_3O_4S$: C 33.17; H 3.25; N 19.34; S 14.76.

NMR (DMSO-TFA): 3.98 (3H, s,=NOCH$_3$), 7.2 (1H, s, 5-H on thiazoline ring), 9.5 (1H, br-s, =NH), 13.35(2H, s, —OH and —COOH).

Preparation 3

2-[2-(N-chloroacetyl)-imino-3-methoxy-4-thiazolinyl]-2-methoxyimino acetic acid (syn-isomer).

To a solution of benzhydryl ester of 2-[2-(N-chloroacetyl)-imino-3-hydroxy-4-thiazolinyl]-2-methoxyimino acetic acid (4.5 g) and NaHCO$_3$ (0.924 g) in acetone (200 ml) and water (5 ml), methyl iodide (3.1 ml) was added. After stirring for 2 hours at room temperature another portion of NaHCO$_3$ (0.92 g) and methyl iodide (9.3 ml) were added, and the mixture was stirred for 1 hour at room temperature. The reaction mixture was evaporated under reduced pressure until the acetone and the excess of methyl iodide had been pumped off.

The residue was taken up with ethyl ether; the ethereal solution was washed with a saturated aqueous solution of NaHCO$_3$, then with water, dried, and evaporated to dryness, thus giving 4.89 g (100%) of the crude benzhydryl ester of 2-[2-(N-chloroacetyl)-imino-3-methoxy-4-thiazolinyl]-2-methoxyimino acetic acid, as a solid white foam, NMR (CDCl$_3$): 3.8 (3H, s, —NOCH$_3$ on thiazoline ring), 4.01 (3H, s, >C=NOCH$_3$), 4.28 (2H, s, —COCH$_2$Cl), 6.72 (1H, s, —CHPh$_2$), 7.02 (1H,s,5-H on thiazoline ring), 7.31 (1OH, s, —Ph$_2$).

To a stirred solution of the above-prepared ester (4.89 g) and anisole (5 ml) in anhydrous methylene chloride (5 ml), cooled at 0° C., trifluoroacetic acid was added to two portions of 5 ml at an interval of 5 minutes.

After stirring for 20 minutes at 0° C. 1,2-dichloroethane (250 ml) was added; the reaction mixture was evaporated under reduced pressure.

The residue was taken up with acetone and evaporated to dryness, the resulting foam taken up with ethyl ether, diluted with isopropylether and then concentrated to a small volume and filtered, thus giving 2.1 g (70%) of the title compound as a white powder, m.p.=129°–130° C. (dec.), NMR (DMSO-d$_6$) 3.99 (3H, s, —NOCH$_3$ on thiazoline ring), 4.02 (3H, s, —C=NOCH$_3$), 4.4 (2H, s, —COCH$_2$Cl), 7.31 (1H, s, 5-H on thiazoline ring).

Preparation 4

Ethyl 2-[2-imino-3-hydroxy-4-thiazolinyl]-2-methoxyiminoacetate. To a solution of ethyl 4-chloro-2-methoxyimino-3-oxo-butyrate (2.07 g) in acetonitrile (30 ml), potassium thiocyanate (2.91 g) was added and the mixture was stirred for 12 hours at room temperature. The potassium chloride precipitated was filtered off and the solution was evaporated to dryness under vacuum. To the residue dissolved in N,N-dimethylacetamide (10 ml) hydroxylamine hydrochloride (2.085 g) was added, and the solution stirred overnight at 60° C.

Ethyl ether (40 ml) was added to the solution, after stirring for 15 minutes, the precipitate was collected by filtration.

The solid was dissolved in water, the solution was brought to pH 5 with aqueous solution of NaHCO$_3$, then evaporated under reduced pressure.

The residue was triturated with chloroform, filtered from undissolved matter, the filtrate was evaporated to dryness, thus giving the crude title compound as a brownish oil, NMR (CDCl$_3$): 1.25 (3H, t,—OCH$_2$CH$_3$), 3.90 (3H, s, =NOCH$_3$), 4.25 (2H, q,—OCH$_2$—CH$_3$), 6.73 (1H, s, 5-H on thiazoline ring), 6.9 (2H, br-s, =NH and —OH).

Preparation 5

Ethylester of 2-(2-imino-3-amino-4-thiazolinyl)-2-methoxyimino acetic acid (syn-isomer).

O-mesitylenesulfonylhydroxylamine (2.15 g) was added to a stirred suspension, cooled at 0° C., of ethyl ester of 2-(2-amino-4-thiazolyl)-2-methoxyimino acetic acid (2.29 g) in methylene chloride (100 ml), giving a complete dissolution of the reaction mixture. After stirring for 10 minutes at 0° C. and 30 minutes at room temperature a white solid was formed.

After adding ethyl ether (20 ml) the solid was collected, washed with ethyl ether thus giving 3.9 g (87%) of the mesitylene sulfonate of the ethyl ester of 2-(2-imino-3-amino-4-thiazolinyl)-2-methoxyimino acetic acid: m.p.=223°-224° C.

NMR (d$_6$-DMSO): 1.25 (3H, t, —OCH$_2$CH$_3$), 2.15 (3H, s, p—CH$_3$ on mesitylene sulfonate), 2.50 (6H, s, o—CH$_3$ on mesitylene sulfonate), 3.98 (3H, s, N=OCH$_3$), 4.25 (2H, q, —OCH$_2$CH$_3$), 6.0 (2H, br-s, —NH$_2$), 6.7 (2H, s, m-H on mesitylene sulfonate), 7.18 (1H, s, 5-H on thiazoline ring), 9.5 (2H, br-s, =NH, H+).

To a stirred suspension of the above prepared salt (4.44 g) in H$_2$O (20 ml) and ethyl acetate (50 ml) a few drops of saturated aqueous solution of Na$_2$CO$_3$ were added, obtaining the complete dissolution of the reaction mixture. The mixture was extracted twice with ethyl acetate.

The combined ethyl acetate solutions were washed with a saturated aqueous sodium chloride solution, separated, dried and evaporated to dryness, giving an oily residue, which was triturated with ethyl ether thus giving 1.96 g (80%) of the title compound: m.p.=104°-105° C.

T.L.C. (CHCl$_3$:MeOH:HCOOH=100:70:30): a single spot

NMR (d$_6$-DMSO): 1.25 (3H, t, —OCH$_2$CH$_3$), 3.95 (3H, s, N=OCH$_3$), 4.25 (2H, q, —OCH$_2$CH$_3$), 5.0 (2H, s, —NH$_2$), 6.35 (1H, s, 5-H on thiazoline ring).

Preparation 6

2-(2-tritylimino-3-amino-4-thiazolinyl)-2-methoxyimino acetic acid (syn-isomer).

O-mesitylenesulfonylhydroxylamine (1.3 g.) was added at room temperature to a stirred suspension of 2-(2-tritylamino-4-thiazolyl)-2-methoxyimino acetic acid (2.15 g) in methylene chloride (40 ml), thus giving in a few minutes the complete dissolution of the reaction mixture. Stirring was maintained for 18 hours, during which time the mesitylenesulfonic salt of the title compound slowly separates as a white solid. The product was filtered and washed with ethyl ether, thus giving 2.98 g (92%) of 2-(2-tritylimino-3-amino-4-thiazolinyl)-2-methoxyimino acetic acid, mesitylene sulfonate, m.p.=161°-163° dec.

This salt crystallizes nicely from acetone, retaining ½ molecule of the solvent; m.p.=170° dec.

NMR (d$_6$-DMSO): 2.1 (3H, s, p—CH$_3$ on mesitylene sulfonate), 2.16 (3H, s, CH$_3$ of Me$_2$CO), 2.50 (6H, s, o—CH$_3$ on mesitylene sulfonate), 3.98 (3H, s, =N—OCH$_3$), 6.73 (2H, s,m-H on mesitylene sulfonate), 6.9-7.2 (18H, broad m, H-on trityl, 5-H on thiazoline, —NH$_2$), ~8.2 (2H, broad s, =NH, H+).

To a stirred suspension of the above-prepared salt (6.44 g) in water (50 ml), aqueous 2 N NaOH was added until complete dissolution (~pH 14) occurred.

The yellowish solution was slowly brought to pH 6.5 with aqueous 8% HCl: the title compound (as an internal salt) separates as a voluminous white gel.

This mixture was heated 15 minutes on a steam bath, in order to facilitate the filtration of the product from the mother aqueous liquors. The collected material was thoroughly washed with distilled water and then dried overnight at 75° C. under reduced pressure, thus giving 3.59 g (~81%) of 2-(2-tritylimino-3-amino-4-thiazolinyl)-2-methoxyimino acetic acid as an amorphous white substance (water still retained).

Crystallization of this product from absolute ethanol afforded pure crystalline material (with 1 molecule of EtOH, as detected by NMR and elemental analysis), m.p.: 157° (dec.)

NMR (d$_5$-pyridine): 3.9 (3H, s, N=OH), 6.39 (1H, s, 5-H on thiazoline ring), 7.07–7.6 (15H, two multiplets centered at 7.2 and 7.5 ppm, trityl), 8.0 (2H, s, NH$_2$).

Preparation 7

2-[2-(N-chloroacetyl)-imino-3-hydroxy-4-thiazolinyl]-2-methoxyimino acetic acid (syn-isomer)

To an ice-cold solution of maleic anhydride (13.72 g) in chloroform (200 ml), 36% H$_2$O$_2$ (26.5 ml) was added and the mixture was stirred for 2 hours at 0° C. Ethyl 2-[2-(N-chloroacetyl)-amino-4-thiazolyl-2-methoxyimino acetate (30.57 g) was added dropwise. After stirring for 16 hours at room temperature, the organic phase was washed with 200 ml of 2% aqueous NaHCO$_3$ solution, then with water, dried and evaporated under reduced pressure. The residue was crystallized from 95% ethanol, thus giving ethyl-2-[2-(N-chloroacetyl)-imino-3-hydroxy-4-thiazolinyl]-2-methoxyimino acetate (24 g), m.p. 149°–150° C.

Elemental analysis: Found: C 37.15; H 3.80; N 12.86; Cl 11.07; S 9.78; calculated for C$_{10}$H$_{12}$ClN$_3$O$_5$S: C 37.33; H 3.76; N 13.06; Cl 11.02; S 9.96.

T.L.C. (CHCl$_3$:CH$_3$OH:HCOOH=180:20:2): R$_f$=0.51.

N.M.R. (DMSO-d$_6$): 1.26 (3H, t, —OCH$_2$CH$_3$), 4.05 (3H, s, =N—OCH$_3$), 4.32 (2H, q, —OCH$_2$CH$_3$), 4.56 (2H, s, —COCH$_2$Cl); 5.87 (1H, br-s, —OH), 7.77 (1H, s, 5-H on thiazoline ring).

To a suspension of the above prepared ester (16.08 g) in dry ethanol (100 ml), 35% NaOH (8.5 ml) was added dropwise, while the temperature was kept at 20°-22° C. The mixture was then stirred for 8 hours at 20°-22° C. The solid was filtered, washed with dry ethanol and dissolved in water (100 ml). The solution, cooled at 0° C., was acidified, under stirring, with 37% HCl (8.25 ml). The solid precipitated was collected by filtration, washed with a small amount of cold water, dried, thus giving 11.15 g (76%) of the title compound, m.p. 157° C. (dec.).

Elemental analysis; Found: C 32.52; H 2.73; N 14.03; S 10.64; calculated for C$_8$H$_8$ClN$_3$O$_5$S: C 32.71; H 2.74; N 14.31; S 10.91.

N.M.R. (DMSO-d$_6$): 3.98 (3H, s, =NOCH$_3$), 4.5 (2H, s, —COCH$_2$Cl), 7.0 (2H, br-s, —OH and —COOH), 7.5 (1H, s, 5-H on thiazoline ring).

Preparation 8

2-[2-(N-chloroacetyl)-imino-3-hydroxy-4-thiazolinyl]-2-[2-tert-butoxycarbonyl-prop-2-yl-oxyimino)-acetic acid (syn-isomer)

To a suspension of ethyl ester of 2-[2-(N-chloroacetyl)-amino-4-thiazolyl]-2-(2-tert-butoxycarbonyl-prop-2-yl-oxyimino)-acetic acid (5 g) in dry ethanol (30 ml), 35% NaOH (3.5 ml) was added dropwise and the mixture was stirred for 6 hours at 25° C. After removing the solvent under vacuum, the residue was taken up with water, stratified with ethyl acetate and acidified with 37% HCl (4 ml). The organic layer was washed with water, dried on Na$_2$SO$_4$ and evaporated to dryness, thus giving 4.1 g (89%) of 2-[2-(N- chloroacetyl)-amino-4-thiazolyl]-2-(2-tert-butoxycarbonyl-prop-2-yl-oxyimino)-acetic acid. To a solution of this acid (4.1 g) in dimethylformamide (20 ml), cooled at 10° C., triethylamine (1.4 ml) and then bromoacetone (1.66 g) were added. The solution was stirred for 24 hours at 0° C., then dropped into ice-water, the solid precipitated was filtered and chromatographed (silica gel) using cyclohexane-ethyl acetate (2:1) as eluent to yield 3.27 g of the acetonyl ester of 2-[2-(N-chloroacetyl)-amino-4-thiazolyl]-2-(2-tert-butoxycarbonyl-prop-2-yl-oxyimino)-acetic acid.

N.M.R. (DMSO-d$_6$) 1.35 (9H, s, O—C(CH$_3$)$_3$), 1.45 (6H, s,

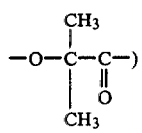

2.17 (3H, s,

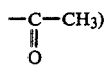

4.20 (2H, s, —COCH$_2$Cl), 4.76 (2H, s, —OCH$_2$CO—), 7.50 (1H, s, 5-H on thiazole ring).

To a solution of maleic anhydride (0.9 g) in chloroform (40 ml), cooled at 0° C., 36% H$_2$O$_2$ (1.7 ml) was added. After stirring for 2 hours at 0° C., the above prepared ester (3 g) was added to the solution and the mixture was stirred for 65 hours at 0° C. The organic phase was washed with an aqueous NaHCO$_3$ solution, then with water, dried and evaporated to dryness. The residue was crystallized from ethyl ether-petroleum ether, thus giving 2.5 g (80%) of the acetonyl ester of 2-[2-(N-chloroacetyl)-imino-4-thiazolinyl]-2-(2-tert-butoxycarbonyl-prop-2-yl-oxyimino)-acetic acid.

To an ice-cold solution of this ester (2 g) in tetrahydrofuran (110 ml) and water (35 ml), 0.1 N NaOH (83 ml) was added in 20 minutes. After stirring for 30 minutes, the reaction mixture was acidified with 1 N HCl (8.3 ml) and concentrated to about 110 ml under reduced pressure and then extracted with ethyl acetate, the organic phase was dried and evaporated under reduced pressure. The residue was crystallized from ethyl ether thus giving 1.2 g (68%) of the title compound, m.p. 155° C. (dec.).

Elemental analysis; Found: C 42.46; H 4.77; N 9.78; Cl 8.51; S 7.62; calculated for C$_{15}$H$_{20}$ClN$_3$O$_7$S: C 42.71; H 4.78; N 9.96; Cl 8.40; S, 7.60.

N.M.R. (DMSO-d$_6$): 1.42 (9H, s, —OC(CH$_3$)$_3$), 1.47 (6H, s,

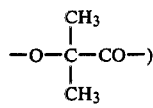

4.51 (2H, s, —COCH$_2$Cl), 7.48 (1H, s, 5-H on thiazoline ring).

Preparation 9

2-[2-(N-chloroacetyl)-imino-3-hydroxy-4-thiazolinyl]-2-methoxyimino acetic acid (anti-isomer)

A solution of 2-[2-(N-chloroacetyl)-imino-3-hydroxy-4-thiazolinyl]-2-methoxyimino acetic acid (syn-isomer) (2 g) in dry tetrahydrofuran (250 ml) cooled at 0° C. was saturated with gaseous HCl and then maintained for 3 hours at room temperature. After evaporating to dryness under reduced pressure, the residue was treated with water (20 ml); the solution was cooled to 5° C., the solid precipitated was collected, washed with a small amount of cold water and dried under vacuum to yield 1.4 g (70%) of the title compound, m.p. 169°–171° C. (dec.).

Elemental analysis; Found: C 32.81; H 2.84; N 14.16; S 10.72; calculated for C$_8$H$_8$ClN$_3$O$_5$S: C 32.71; H 2.74; N 14.31; S 10.91.

N.M.R. (DMSO-d$_6$): 4.07 (3H, s, =NOCH$_3$), 4.51 (2H, s, —COCH$_2$Cl), 7.61 (1H, s, 5-H on thiazoline ring).

Preparation 10

2-[2-(N-chloroacetyl)-imino-3-hydroxy-4-thiazolinyl]-2-ethoxyimino acetic acid (syn-isomer)

To an ice-cold solution of maleic anhydride (2.5 g) in chloroform (45 ml), 36% H$_2$O$_2$ (4.7 ml) was added and the mixture was stirred for 2 hours at room temperature. Ethyl 2-[2-(N-chloroacetyl)-amino-4-thiazolyl-2-ethoxyimino acetate (5.8 g) was added and the mixture was stirred for 18 hours at room temperature. The organic phase was washed with 50 ml of 5% aqueous NaHCO$_3$ solution, dried on Na$_2$SO$_4$ and evaporated to dryness under vacuum. The residue was crystallized from ethanol to afford 4.8 g (79%) of ethyl 2-[2-(N-chloroacetyl)-imino-3-hydroxy-4-thiazolinyl]-2-ethoxyimino acetate (syn-isomer).

To a suspension of the above prepared ester (2 g) in dry ethanol (25 ml), 35% NaOH (2 ml) was added, under stirring at room temperature, obtaining a complete solution, followed by precipitation of the sodium salt. After stirring for 7 hours at room temperature, the solid was filtered, washed with 99% ethanol, with ethyl ether and dried. The solution of the sodium salt in water (20 ml), cooled to 5° C., was acidified with 37% HCl (1 ml). The solid precipitated was collected by filtration to afford 1.3 g (71%) of the title compound, m.p. 138°–140° C. (dec.).

Elemental analysis; Found: C 35.32; H 3.36; N 13.42; S 10.27; calculated for C$_9$H$_{10}$ClN$_3$O$_5$S: C 35.13; H 3.27; N 13.66; Cl 11.52; S 10.42.

N.M.R. (DMSO-d$_6$): 1.25 (3H, t, —OCH$_2$C$\underline{H}_3$), 4.20 (2H, q, —OC$\underline{H}_2$—), 4.36 (2H, s, —COCH$_2$Cl), 7.38 (1H, s, 5-H on thiazoline ring), 11.50 (2H, s, —OH and —COOH).

Preparation 11

2-[2-(N-chloroacetyl)-imino-3-hydroxy-4-thiazolinyl]-2-propoxyimino acetic acid (syn-isomer) was prepared by using the method reported in preparation 10.

Elemental analysis: Found: C 37.30; H 3.72; N 12.97; S 9.77; calculated for: C$_{10}$H$_{12}$ClN$_3$O$_5$S: C 37.33; H 3.76; N 13.06; S 9.97.

N.M.R. (DMSO-d$_6$): 0.91 (3H, t, —OCH$_2$CH$_2$CH$_3$), 1.70 (2H, m, —OCH$_2$C$\underline{H}_2$CH$_3$), 4.20 (2H, t, —OC$\underline{H}_2$CH$_2$CH$_3$), 4.36 (2H, s, —COCH$_2$Cl), 7.38 (1H, s, 5-H on thiazoline ring), 11.6 (2H, s, —OH and —COOH).

Preparation 12

2-[2-(N-formyl)-imino-3-methoxy-4-thiazolinyl]-2-methoxyimino acetic acid (syn-isomer)

To a suspension of 2-[2-(N-formyl)-amino-4-thiazolyl]-2-methoxyimino acetic acid (20 g) in acetonitrile (150 ml), cooled at 0° C., a solution of diphenyldiazomethane (17 g) in acetonitrile was added dropwise. After stirring for 30 minutes at room temperature, the solid was filtered, washed with acetonitrile, then dissolved in chloroform; the solution was washed with aqueous sodium bicarbonate solution, dried and evaporated to dryness. The residue was triturated with dry ethanol, filtered, dried thus giving 25 g (80%) of the benzhydryl ester, m.p. 158°–160° C.

N.M.R. (CDCl$_3$): 3.95 (3H, s, —OCH$_3$), 6.83 (1H, 5-H on thiazole ring), 7.1 (1H, s, —CHPh$_2$), 7.3 (10H, s, Ph$_2$), 8.7 (1H, s,

75% m-chloroperbenzoic acid (13.9 g) was added portionwise to a solution of the above-prepared ester (16 g) in chloroform (48 ml) under cooling to 0° C. After stirring for 16 hours at room temperature, the reaction mixture was cooled, m-chlorobenzoic acid precipitated was filtered off, the filtrate was evaporated to dryness under vacuum, the residue was crystallized from ethyl ether, thus giving 13.28 g (80%) of the benzhydryl ester of 2-[2-(N-formyl)-imino-3-hydroxy-4-thiazolinyl]-2-methoxyimino acetic acid, m.p. 172° C. (dec.).

N.M.R. (CDCl$_3$): 4.03 (3H, s, =NOCH$_3$), 7.03 (1H, s, 5-H on thiazoline ring), 7.12 (1H, s, —CHPh$_2$), 7.2–7.35 (10H, m, Ph$_2$), 8.04 (1H, s,

To a solution of this ester (7.1 g) in dimethylformamide (50 ml) and water (5 ml), KHCO$_3$ (1.7 g) and CH$_3$I (5.8 ml) were added. After stirring for 16 hours at room temperature the reaction mixture was poured into 300 ml of ice-water. The solid precipitated was collected, dried and chromatographed on silica gel using ethyl acetate-cyclohexane (1:1.5) as eluent to yield 5.8 g of the benzhydryl ester of 2-[2-(N-formyl)-imino-3-methoxy-4-thiazolinyl]-2-methoxyimino acetic acid.

To a solution of this ester (2 g) in CH$_2$Cl$_2$ (3 ml) and anisole (1 ml), cooled at 0° C., cold trifluoroacetic acid (8 ml) was added; the mixture was stirred for 30 minutes at 0° C. and then evaporated to dryness under vacuum. The residue was crystallized from tetrahydrofuran, thus giving 0.90 g (74%) of the title compound, m.p. 163°–164° C.

Elemental analysis; Found: C 36.89; H 3.37; N 16.11; calculated for C$_8$H$_9$N$_3$O$_5$S: C 37.06; H 3.50; N 16.21.

N.M.R. (DMSO-d$_6$): 4.01 (3H, s, =NOCH$_3$), 4.08 (3H, s, —OCH$_3$), 7.35 (1H, s, 5-H on thiazoline ring), 8.86 (1H, s,

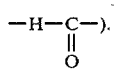

Preparation 13

Ethyl-2-[2-(N-formyl)-imino-3-ethoxy-4-thiazolinyl]-2-methoxyimino acetate (syn-isomer)

To a solution of ethyl 2-[2-(N-formyl)-imino-3-hydroxy-4-thiazolinyl]-2-methoxyiminoacetate (5.5 g) in acetone (200 ml) and water (20 ml), KHCO$_3$ (2.4 g) and ethyl iodide (6.3 g) were added. The mixture was stirred for 2 hours at room temperature; another portion of ethyl iodide (6.3 g) was added and the reaction mixture was stirred for additional 2 hours at room temperature. Acetone and the excess of ethyl iodide were removed under reduced pressure; the residue was taken up with ethyl ether; the ethereal solution was washed with 5% aqueous sodium bicarbonate solution, then with water, dried and evaporated to dryness, under vacuum. The residue was crystallized from ethyl ether-petroleum ether, thus giving 5.3 g of the title compound.

Elemental analysis; Found: C 43.94; H 4.98; N 13.78; S 10.46; calculated for C$_{11}$H$_{15}$N$_3$O$_5$S: C 43.85; H 5.02; N 13.95; S 10.64.

N.M.R. (CDCl$_3$): 1.25 (3H, t, —OCH$_2$CH$_3$), 1.3 (3H, t, —OCH$_2$CH$_3$), 3.96 (3H, s, =NOCH$_3$), 4.24 (2H, q, —OCH$_2$CH$_3$), 4.30 (2H, q, —OCH$_2$CH$_3$), 6.79 (1H, s, 5-H on thiazoline ring), 8.76 (1H, s,

Preparation 14

2-[2-(N-chloroacetyl)-imino-3-isopropylidene-amino-4-thiazolinyl]-2-methoxyimino acetic acid (syn-isomer)

O-mesitylenesulfonylhydroxylamine (2.8 g) was added at room temperature to a stirred solution of benzhydryl ester of 2-[2-(N-chloroacetyl)-amino-4-thiazolyl]-2-methoxyimino acetic acid (4,44 g) in chloroform (50 ml). Stirring was maintained for 2 hours. The solvent was evaporated under reduced pressure, the residue was triturated with ethyl ether, filtered and dried, thus giving 5.62 g (85%) of benzhydryl ester of 2-[2-(N-chloroacetyl)-imino-3-amino-4-thiazolinyl]-2-methoxyimino acetic acid, mesitylene sulfonate.

A stirred solution of the above-prepared salt (4 g) in acetone (35 ml) was refluxed for 10 minutes and then evaporated to dryness. The residue was suspended in ethyl acetate. The suspension was treated with saturated aqueous NaHCO$_3$ solution; the organic layer was washed with water, dried and evaporated to dryness. The residue was crystallized from ethanol, thus giving 2.6 g (80%) of the benzhydryl ester of 2-[2-(N-chloroacetyl)-imino-3-(2-isopropylideneimino)-4-thiazolinyl]-2-methoxyimino acetic acid, m.p. 137°–139° C.

To an ice-cold solution of trifluoroacetic acid (10 ml), anisole (1 ml) and acetone (1.5 ml), the above-prepared ester (1.675 g) was added portionwise at 5° C. After stirring for 20 minutes at room temperature, the reaction mixture was evaporated to small volume, acetone was added and then evaporated to dryness. The residue was washed several times with ethyl ether thus giving 1.01 g (90%) of the title compound, m.p. 133°–134° C. (dec.).

Elemental analysis; Found: C 39.51; H 4.00; N 9.50; Cl 16.68; S 10.46; calculated for $C_{11}H_{13}ClN_4O_4S$: C 39.70; H 3.93; N 9.63; Cl 16.83; S 10.65.

N.M.R. (DMSO-d$_6$): 1.84 and 2.22 (6H, 2s,

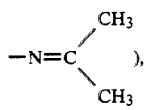

3.98 (3H, s, =NOCH$_3$), 4.35 (2H, s, —COCH$_2$Cl), 7.52 (1H, s, 5-H on thiazoline ring).

EXAMPLE 1

7β-[2-(2-imino-3-hydroxy-4-thiazolinyl)-2-methoxyminoacetamido]-3-acetoxymethyl-3-cephem-4-carboxylic acid (syn-isomer)

To a suspension of 2-[2-(N-chloroacetyl)-imino-3-hydroxy-4-thiazolinyl]-2-methoxyimino acetic acid (2.6 g) in anhydrous THF (150 ml) 7-amino-cephalosporanic acid, tert-butyl ester (2.97 g) was added under cooling at 5° C. and afterwards dropwise a solution of N,N'-dicyclohexyl carbodiimide (1.92 g) in anhydrous THF (30 ml). The reaction mixture was stirred for 3 hours at room temperature, then was filtered off from the separated solid, viz. dicyclohexylurea. The filtrate was evaporated to dryness, the residue was taken up with ethyl acetate, the solid was filtered off, the filtrate was evaporated to dryness; the residue was taken up with ethyl ether, the precipitated product was filtered, washed with ethyl ether, thereby giving 4.65 g (85%) of crude product.

This was dissolved in CHCl$_3$ (50 ml) and absorbed on a chromatography column of silica gel; the product was then eluted using a mixture of chloroform (300 ml) and ethanol (40 ml).

The eluate was concentrated to a small volume and added to ethyl ether, thus precipitating pure tert-butyl 7-β-[2-(2-chloroacetylimino-3-hydroxy-4-thiazolinyl)-2-methoxyimino-acetamido]-3-acetoxymethyl-3-cephem-4-carboxylate. A solution of this ester (1.495 g) and thiourea (0.188 g) in N,N-dimethylacetamide (10 ml) was stirred for 2 hours at room temperature.

The solution was then diluted with ethyl acetate; a gummy material precipitated, the supernatant solvent was discarded and the residue was carefully triturated with fresh ethyl acetate until a powder was obtained. The product was collected by filtration, thus giving the tert-butyl ester of 7-β-[2-(2-imino-3-hydroxy-4-thiazolinyl)-2-methoxyimino-acetamido]-3-acetoxymethyl-3-cephem-4-carboxylic acid (1.1 g).

A solution of this compound (0.785 g) in trifluoroacetic acid (15 ml) was stirred for 70 minutes at room temperature. The solvent was then evaporated to dryness under reduced pressure, the residue was taken up with acetone, filtered off from undissolved material, the filtrate was evaporated to dryness, and the residue triturated with ethyl ether, thus giving the title compound (as trifluoroacetic salt).

This salt was dissolved again in acetone.

A calculated amount of potassium ethyl hexanoate (about 1 equivalent) in acetone was added, thus giving the precipitation of the title product (as internal salt): 0.6 g Elemental Analysis; Found: C 39.98; H 3.72; N 14.47; S 13.40; Calculated for $C_{16}H_{17}N_5O_8S_2$: C 40.76; H 3.63; N 14.85; S 13.60.

IR (KBr) cm$^{-1}$ 3300 NH 1770>C=O β-lactam 1520 —CONH-sec.amide.

T.L.C.: HCOOH: H$_2$O: MeOH: CHCl$_3$ (20:10:70:40) R$_f$=0.64

NMR (d$_6$-DMSO) 2.05 (3H, s, —OCOCH$_3$), 3.95 (3H, s, =NOCH$_3$), 7.1 (1H, s, 5-H on thiazoline ring), 10.7 (1H,d, —CON<u>H</u>).

EXAMPLE 2

7β-[2-(2-imino-3-hydroxy-4-thiazolinyl)-2-methoxyiminoacetamido]-3-[(1-methyl-1,2,3,4-tetrazol-5-yl)-thiomethyl]-3-cephem-4-carboxylic acid (syn-isomer)

N,N'-dicyclohexylcarbodiimide (1.05 g) was added to a cooled (0°-5° C.) solution of 2-[2-(N-chloroacetyl)-imino-3-hydroxy-4-thiazolinyl]-2-methoxyimino acetic acid (1.5 g) in anhydrous THF (100 ml). The mixture was stirred for 10 minutes at 5° C. and 40 minutes at room temperature, giving a turbid solution.

At the same time a suspension of 7-amino-3-[(1-methyl-1,2,3,4-tetrazol-5-yl)-thiomethyl]-3-cephem-4-carboxylic acid (1.85 g), and N,O-bis-(trimethyl-silyl)acetamide (4.58 g) in anhydrous THF (130 ml) CH$_3$CN (50 ml) and DMF (2.5 ml) was stirred for 1 hour at 50° C., until all the solid material was dissolved.

Into this solution, cooled with an ice-bath, the first solution was dropped with stirring.

After stirring for 20 minutes at 0°-5° C. and 90 minutes at room temperature, the reaction mixture was evaporated to dryness under vacuum; the residue was then stirred for 15 minutes with H$_2$O (250 ml) and ethyl acetate (300 ml), and filtered from the insoluble matter.

The organic layer was separated; the solid was suspended in water and extracted again with ethyl acetate. The combined extracts were concentrated to a small volume, thus giving 2.1 g of 7β-[2-(2-N-chloroacetyl-imino-3-hydroxy-4-(thiazolinyl)-2-methoxyimino-acetamido]-3-[(1-methyl-1,2,3,4-tetrazol-5-yl)-thiomethyl]-3-cephem-4-carboxylic acid, collected by filtration as a yellowish powder. A solution of the above-prepared compound (0.790 g) and thiourea (0.1 g) in N,N-dimethylacetamide (5 ml) was stirred for 4 hours at room temperature. The solution was then diluted with ethyl acetate (10 ml), thus giving a gummy material. After discarding the supernatant solvent, the residue was triturated with fresh ethyl acetate until a powder was obtained. The product was collected by filtration thus giving 0.6 g of the crude title compound (mainly as HCl salt).

This product was suspended in distilled water (5 cc.), heated 1 minute at about 60° C. and then cooled a few hours in an ice bath. The solid was filtered, washed thoroughly with water and then dried, so obtaining 0.45 g of the title compound (as internal salt).

Elemental Analysis; Found: C 36.52; H 3.28; N 23.75; S 18.11; Calculated for $C_{16}H_{17}N_9O_6S_3$: C 36.43; H 3.25; N 23.89; S 18.23.

I.R. (KBr): cm$^{-1}$ 1770>C=O β-lactam

T.L.C.: HCOOH: H$_2$O; MeOH: CHCl$_3$ (20:10:70:40) R$_f$=0.61

NMR (d$_6$-DMSO) 3.95–3.97 (6H, 2s., CH$_3$ on tetrazole and=N-OCH$_3$) 7.01 (1H, s., 5-H on thiazoline ring) 10.5 (1H, d, CON<u>H</u>).

EXAMPLE 3

7β-[2-(2-imino-3-hydroxy-4-thiazolinyl)-2-methoxyimino-acetamido]-3-[(tetrazolo[1,5-b]pyridazin-6-yl)-thiomethyl]-3-cephem-4-carboxylic acid (syn-isomer)

N,N'-dicyclohexylcarbodiimide (0.63 g) was added to a cooled (0°–5° C.) solution of 2-[2-(N-chloroacetyl)-imino-3-hydroxy-4-thiazolinyl]-2-methoxyimino acetic acid (1.5 g) in anhydrous THF (75 ml). The mixture was stirred for 15 minutes at 0° C. and 30 minutes at 15° C. obtaining a turbid solution.

At the same time a suspension of 7-amino-3-[(tetrazolo[1,5-b]pyridazin-6-yl)-thiomethyl]-3-cephem-4-carboxylic acid (0.93 g), and N,O-bis-(trimethyl-silyl-)acetamide (1.23 ml) in anhydrous THF (20 ml) and CH$_3$CN (14 ml) was stirred for 30 minutes at 50° C., until all the solid material was dissolved.

Into this solution, cooled to −10° C., the first solution was dropped with stirring in 10 minutes.

After stirring for 90 minutes at room temperature, the reaction mixture was evaporated to dryness under vacuum; the residue was then stirred for 15 minutes with H$_2$O (50 ml) and ethyl acetate (100 ml), filtered from the insoluble matter.

The organic layer was separated; the solid was suspended in water and extracted again with ethyl acetate. The combined extracts were concentrated to a small volume thus giving 1.4 g of 7β-[2-(2-N-chloroacetyl-imino-3-hydroxy-4-(thiazolinyl)-2-methoxyimino-acetamido]-3-[(tetrazolo[1,5-b]pyridazin-6-yl)-thiomethyl]-3-cephem-4-carboxylic acid, collected by filtration as a yellowish powder. A solution of the above-prepared compound (0.840 g) and thiourea (0.1 g) in N,N-dimethylacetamide (4 ml) was stirred for 2 hours at room temperature. The solution was then diluted with ethyl acetate (10 ml) to obtain a gummy material. After discarding the supernatant solvent, the residue was triturated with fresh ethyl acetate until a powder was obtained. The product was collected by filtration thus giving 0.7 g of the crude title compound (mainly as HCl salt).

This product was suspended in distilled water (25 ml), the pH was brought to 5 by adding NaHCO$_3$; the insoluble matter was filtered off; the filtrate was acidified with 8% HCl to pH 2.5; the solid precipitated was filtered, washed with a small amount of water, with ethanol, with ethyl ether and then dried, so obtaining 0.98 g of the title compound.

Elemental analysis; Found: C, 37.97; H 2.85; N 24.62; S 16.81; Calculated for C$_{18}$H$_{16}$N$_{10}$O$_6$S$_3$: C 38.29; H 2.86; N 24.81; S 17.04.

T.L.C.: HCOOH: MeOH: CHCl$_3$ (20:40:160): R$_f$=0.25

NMR (d$_6$-DMSO) 7.01 (1H, s, 5-H on thiazoline ring), 7.75 (1H,d, 8-H on the pyridazine ring), 8.57 (1H, d, 7-H on the pyridazine ring), 10.5 (1H, d, -CONH).

IR (KBr) cm$^{-1}$ 1770>C=O β-lactam

EXAMPLE 4

7β-[2-(2-imino-3-hydroxy-4-thiazolinyl)-2-methoxyimino-acetamido]-3-[(5-methyl-1,3,4-thiadiazol-2-yl)-thiomethyl]-3-cephem-4-carboxylic acid (syn-isomer) was obtained by using the method reported in example 2.

Elemental analysis; Found: C 37.21; H 3.22; N 17.90; S 23.21; Calculated for C$_{17}$H$_{17}$N$_7$O$_6$S$_4$: C 37.56; H 3.15; N 18.04; S 23.59.

T.L.C.: HCOOH: MeOH: CHCl$_3$ (30:70:160) R$_f$=0.61

IR (KBr) cm$^{-1}$ 1770>C=O β-lactam

NMR (d$_6$-DMSO) 2.7 (3H, s, CH$_3$ on thiadiazole ring), 3.98 (3H, s., =N-OCH$_3$), 7.1 (1H, s., 5-H on thiazoline ring), 10.1 (1H, d., CONH).

EXAMPLE 5

7β-[2-(2-imino-3-hydroxy-4-thiazolinyl)-2-methoxyimino-acetamido]-3-[1-(2-cyanoethyl-1,2,3,4-tetrazol-5-yl)-thiomethyl]-3-cephem-4-carboxylic acid (syn-isomer) was prepared by using the method reported in example 2.

Elemental Analysis; Found: C 38.72; H 3.31; N 24.57; S 16.75; calculated for C$_{18}$H$_{18}$N$_{10}$O$_6$S$_3$: C 38.16; H 3.20; N 24.72; S 16.98.

I.R. (KBr) 1770 cm$^{-1}$>C=O β-lactam

T.L.C.: HCOOH: MeOH: CHCl$_3$ (30:70:160): R$_f$=0.58

NMR (d$_6$-DMSO) 3.19 (2H, t, -CH$_2$CN), 3.97 (3H, s, O-CH$_3$), 4.64 (2H, t, -C$_2$-CH$_2$CN), 7.12 (1H, s, 5-H on thiazoline ring), 9.8 (1H, d, -CONH-).

EXAMPLE 6

7β-[2-(2-imino-3-hydroxy-4-thiazolinyl)2-methoxymino-acetamido]-3-[(8-amino-6-tetrazolo[1,5-b]pyridazinyl)-thio methyl]-3-cephem-4-carboxylic acid (syn-isomer) was obtained by using the method reported in example 2.

Elemental Analysis; Found: C 37.52; H 3.01; N 25.99; S 16.27; Calculated for C$_{18}$H$_{17}$N$_{11}$O$_6$S$_3$; C 37.30; H 2.96; N 26.58; S 16.59.

T.L.C.: HCOOH: MeOH: CHCl$_3$ (30:70:160): R$_f$=0.50

I.R. (KBr) 1770 cm$^{-1}$: >C=O β-lactam

NMR (d$_6$-DMSO): 3.97 (3H, s, =N-OCH$_3$), 6.39 (1H, s, 7-H on pyridazine ring), 7.12 (1H, s, 5-H on thiazoline ring), 7.98 (2H,br-s, 8-NH$_2$ on pyridazine ring), 9.8 (1H, d, -CONH).

EXAMPLE 7

Using the method reported in example 2 also the following compounds were obtained:

7β-[2-(2-imino-3-hydroxy-4-thiazolinyl)-2-hydroxyimino-acetamido]-3-cephem-4-carboxyic acid (syn-isomer);

7β-[2-(2-imino-3-hydroxy-4-thiazolinyl)-2-methoxyimino-acetamido]-3-cephem-4-carboxylic acid (syn-isomer);

7β-[2-(2-imino-3-hydroxy-4-thiazolinyl)-2-methoxyimino-acetamido]-1(R)-sulphoxide-3-cephem-4-carboxylic acid (syn-isomer);

7β-[2-(2-imino-3-hydroxy-4-thiazolinyl)-2-methyl-imino-acetamido]-1(S)-sulphoxide-3-cephem-4-carboxylic acid (syn-isomer);

7β-[2-(2-imino-3-hydroxy-4-thiazolinyl)-2-methoxyimino-acetamido]-3-chloro-3-cephem-4-carboxylic acid (syn-isomer);

7β-[2-(2-imino-3-hydroxy-4-thiazolinyl)-2-methoxyimino-acetamido]-3-hydroxy-3-cephem-4-carboxylic acid (syn-isomer);

7β-[2-(2-imino-3-hydroxy-4-thiazolinyl)-2-methoxyimino-acetamido]-3-methoxy-3-cephem-4-carboxylic acid (syn-isomer);

7β-[2-(2-imino-3-methoxy-4-thiazolinyl)-2-methoxyimino-acetamido]-3-cephem-4-carboxylic acid (syn-isomer);

7β-[2-(2-imino-3-hydroxy-4-thiazolinyl)-2-methoxy-imino-acetamido]-1(R)-sulphoxide-3-acetoxymethyl-3-cephem-4-carboxylic acid (syn-isomer);

7β-[2-(2-imino-3-hydroxy-4-thiazolinyl)-2-methoxy-imino-acetamido]-1(S)-sulphoxide-3-acetoxy-methyl-3-cephem-4-carboxylic acid (syn-isomer);

7β-[2-(2-imino-3-amino-4-thiazolinyl)-2-methoxy-imino-acetamido]-3-acetoxy-methyl-3-cephem-4-carboxylic acid (sym-isomer);

7β-[2-(2-imino-3-amino-4-thiazolinyl)-2-methoxy-imino-acetamido]-1(R)-sulphoxide-3-acetoxymethyl-3-cephem-4-carboxylic acid (syn-isomer);

7β-[2-(2-imino-3-amino-4-thiazolinyl)-2-methoxy-imino-acetamido]-1(S)-sulphoxide-3-acetoxy-methyl-3-cephem-4-carboxylic acid (syn-isomer);

7β-[2-(2-imino-3-methoxy-4-thiazolinyl)-2-methoxy-imino-acetamido]-3-acetoxy-methyl-3-cephem-4-carboxylic acid (syn-isomer);

7β-[2-(2-imino-3-methoxy-4-thiazolinyl)-2-methoxy-imino-acetamido]-1(R)-sulphoxide-3-acetoxy-methyl-3-cephem-4-carboxylic acid (syn-isomer);

7β-[2-(2-imino-3-methoxy-4-thiazolinyl)-2-methoxy-imino-acetamido]-1(S)-sulphoxide-3-acetoxy-methyl-3-cephem-4-carboxylic acid (syn-isomer);

7β-[2-(2-imino-3-hydroxy-4-thiazolinyl)-2-methoxy-imino-acetamido]-3-[1-(2-propenyl-1,2,3,4-tetrazol-5-yl)-thiomethyl]-3-cephem-4-carboxylic acid (syn-isomer);

7β-[2-(2-imino-3-hydroxy-4-thiazolinyl)-2-methoxy-imino-acetamido]-3-[(5-methyl-mercapto-1,3,4-thiadiazol-2-yl)-thiomethyl]-3-cephem-4-carboxylic acid (syn-isomer);

7β-[2-(2-imino-3-hydroxy-4-thiazolinyl)-2-methoxy-imino-acetamido]-3-[(8-carboxy-tetrazolo-[1,5-b]-pyridazin-6-yl)-thiomethyl]-3-cephem-4-carboxylic acid (syn-isomer);

7β-[2-(2-imino-3-hydroxy-4-thiazolinyl)-2-methoxy-imino-acetamido]-3-[(8-carboxy methyl-tetrazolo-[1,5-b]-pyridazin-6-yl)-thiomethyl]-3-cephem-4-carboxylic acid (syn-isomer);

7β-[2-(2-imino-3-hydroxy-4-thiazolinyl)-2-methoxy-imino-acetamido]-3-[(2,3-dihydro-2-methyl-3-oxo-1,2,4-triazolo[4,3,b]-pyridazin-6-yl)-thiomethyl]-3-cephem-4-carboxylic acid (syn-isomer);

7β-[2-(2-imino-3-methoxy-4-thiazolinyl)-2-methoxy-imino-acetamido]-3-[(1-methyl-1,2,3,4-tetrazol-5-yl)-thiomethyl]-3-cephem-4-carboxylic acid (syn-isomer);

7β-[2-(2-imino-3-methoxy-4-thiazolinyl)-2-methoxy-imino-acetamido]-3-[1(2-propenyl-1,2,3,4-tetrazol-5-yl)-thiomethyl]-3-cephem-4-carboxylic acid (syn-isomer);

7β-[2-(2-imino-3-methoxy-4-thiazolinyl)-2-methoxy-imino-acetamido]-3-[1-(2-cyanoethyl-1,2,3,4-tetrazol-5-yl)-thiomethyl]-3-cephem-4-carboxylic acid (syn-isomer);

7β-[2-(2-imino-3-methoxy-4-thiazolinyl)-2-methoxy-imino-acetamido]-3-[(5-methyl-1,3,4-thiadiazol-2-yl)-thiomethyl]-3-cephem-4-carboxylic acid (syn-isomer);

7β-[2-(2-imino-3-methoxy-4-thiazolinyl)-2-methoxy-imino-acetamido]-3-[(tetrazolo-[1,5-b]-pyridazin-6-yl)-thiomethyl]-3-cephem-4-carboxylic acid (syn-isomer);

7β-[2-(2-imino-3-methoxy-4-thiazolinyl)-2-methoxy-imino-acetamido]-3-[(8-amino-tetrazolo-[1,5-b]-pyridazin-6-yl)-thiomethyl]-3-cephem-4-carboxylic acid (syn-isomer);

7β-[2-(2-imino-3-methoxy-4-thiazolinyl)-2-methoxy-imino-acetamido]-3-[(8-carboxy-tetrazolo-[1,5-b]-pyridazin-6-yl)-thiomethyl]-3-cephem-4-carboxylic acid (syn-isomer);

7β-[2-(2-imino-3-methoxy-4-thiazolinyl)-2-methoxy-imino-acetamido]-3-[(8-carboxymethyl-tetrazolo-[1,5-b]-pyridazin-6-yl)-thiomethyl]-3-cephem-4-carboxylic acid (syn-isomer);

7β-[2-(2-imino-3-hydroxy-4-thiazolinyl)-2-methoxyimino-acetamido]-1-sulphone-3-cephem-4-carboxylic acid (syn-isomer);

7β-[2-(2-imino-3-hydroxy-4-thiazolinyl)-2-methoxy-imino-acetamido]-1-sulphone-3-acetoxymethyl-3-cephem-4-carboxylic acid (syn-isomer);

7β-[2-(2-imino-3-methoxy-4-thiazolinyl)-2-methoxy-imino-acetamido]-1-sulphone-3-acetoxymethyl-3-cephem-4-carboxylic acid (syn-isomer);

7β-[2-(2-imino-3-hydroxy-4-thiazolinyl)-2-methoxyimino-acetamido]-3-[8-aminocarbonyl-tetrazolo[1,5-b]pyridazin-6-yl-thiomethyl]-3-cephem-4-carboxylic acid (syn-icomer);

7β-[2-(2-imino-3-methoxy-4-thiazolinyl)-2-methoxyimino-acetamido]-3-[8-aminocarbonyl-tetrazolo[1,5-b]pyridazin-6-yl-thiomethyl]-3-cephem-4-carboxylic acid (syn-isomer);

7β-[2-(2-imino-3-amino-4-thiazolinyl)-2-methoxyimino-acetamido]-3-[8-aminocarbonyl-tetrazolo[1,5-b]pyridazin-6-yl-thiomethyl]-3-cephem-4-carboxylic acid (syn-isomer), 7β-[2-(2-imino-3-amino-4-thiazolinyl)2-methoxy-imino-acetamido]-3-cephem-4-carboxylic acid (syn-isomer);

7β-[2-(2-imino-3-hydroxy-4-thiazolinyl)-2-carboxymethoxyimino-acetamido]-3-[(1-methyl-1,2,3,4-tetrazol-5-yl)-thiomethyl]-3-cephem-4-carboxylic acid (syn isomer);

7β-[2-(2-imino-3-hydroxy-4-thiazolinyl)-2-carboxymethoxy-imino-acetamido]-3-[(5-methyl-1,3,4-thiadiazol-2-yl)-thiomethyl]-3-cephem-4-carboxylic acid (syn isomer);

7β-[2-(2-imino-3-hydroxy-4-thiazolinyl)-2-carboxymethoxy-imino-acetamido]-3-[(8-amino-tetrazolo-[1,5-b]-pyridazin-6-yl)-thiomethyl]-3-cephem-4-carboxylic acid (syn isomer);

7β-[2-(2-imino-3-methoxy-4-thiazolinyl)-2-carboxymethoxy-imino-acetamido]-3-[(1-methyl-1,2,3,4-tetrazol-5-yl)-thiomethyl]-3-cephem-4-carboxylic acid (syn isomer);

7β-[2-(2-imino-3-methoxy-4-thiazolinyl)-2-carboxymethoxy-imino-acetamido]-3-[(5-methyl-1,3,4-thiadiazol-2-yl)-thiomethyl]-3-cephem-4-carboxylic acid (syn isomer);

7β-[2-(2-imino-3-methoxy-4-thiazolinyl)-2-carboxymethoxy-imino-acetamido]-3-[(8-amino-tetrazolo-[1,5-b]-pyridazin-6-yl)-thiomethyl]-3-cephem-4-carboxylic acid (syn isomer);

7β-[2-(2-imino-3-hydroxy-4-thiazolinyl)-2-(β)carboxy vinylene-oxy-imino-acetamido]-3-[(8-amino-tetrazolo-[1,5-b]-pyridazin-6-yl)-thiomethyl]-3-cephem-4-carboxylic acid (syn isomer);

7β-[2-(2-imino-3-amino-4-thiazolinyl)-2-methoxy-imino-acetamido]-3-[(1-methyl-1,2,3,4-tetrazol-5-yl)-thiomethyl]-3-cephem-4-carboxylic acid (syn isomer);

7β-[2-(2-imino-3-amino-4-thiazolinyl)-2-methoxy-imino-acetamido]-3-[(5-methyl-1,3,4-thiadiazol-2-yl)-thiomethyl]-3-cephem-4-carboxylic acid (syn isomer);

7β-[2-(2-imino-3-amino-4-thiazolinyl)-2-methoxy-imino-acetamido]-3-[(tetrazolo-[1,5-b]-pyridazin-6-yl)-thiomethyl]-3-cephem-4-carboxylic acid (syn isomer);

7β-[2-(2-imino-3-amino-4-thiazolinyl)-2-methoxy-imino-acetamido]-3-[(8-amino-tetrazolo-[1,5-b]-pyridazin-6-yl)-thiomethyl]-3-cephem-4-carboxylic acid (syn isomer);

7β-[2-(2-imino-3-amino-4-thiazolinyl)-2-carboxymethoxy-imino-acetamido]-3-[(1-methyl-1,2,3,4-tetrazol-5-yl)-thiomethyl]-3-cephem-4-carboxylic acid (syn isomer);

7β-[2-(2-imino-3-amino-4-thiazolinyl)-2-(β)carboxy vinylene-oxy-imino-acetamido]-3-[(1-methyl-1,2,3,4-tetrazol-5-yl)-thiomethyl]-3-cephem-4-carboxylic acid (syn isomer);

7β-[2-(2-imino-3-amino-4-thiazolinyl)-2-methoxy-imino-acetamido]-1-sulphone-3-acetoxymethyl-3-cephem-4-carboxylic acid (syn isomer);

7β-[2-(2-imino-3-hydroxy-4-thiazolinyl)-2-(α-methyl-α-carboxy-ethoxy-imino)-acetamido]-3-acetoxymethyl-3-cephem-4-carboxylic acid (syn isomer);

7β-[2-(2-imino-3-methoxy-4-thiazolinyl)-2-(α-methyl-α-carboxy-ethoxy-imino)-acetamido]-3-acetoxymethyl-3-cephem-4-carboxylic acid (syn isomer);

7β-[2-(2-imino-3-amino-4-thiazolinyl)-2-(α-methyl-α-carboxy-ethoxy-imino)-acetamido]-3-acetoxymethyl-3-cephem-4-carboxylic acid (syn-isomer).

EXAMPLE 8

7β-[2-(2-imino-3-hydroxy-4-thiazolinyl)-2-methoxyimino-acetamido]-3-[(1-methyl-1,2,3,4-tetrazol-5-yl)-thiomethyl]-3-cephem-4-carboxylic acid (syn-isomer)

To a mixture of 7β-[2-(2-imino-3-hydroxy-4-thiazolinyl)-2-methoxyimino-acetamido]-3-acetoxymethyl-3-cephem-4-carboxylic acid (prepared as described in example 1) (120 mg), and 1-methyl-5 mercapto-1,2,3,4-tetrazole sodium salt di-hydrate, (30 mg), in distilled water (7.5 ml), NaHCO$_3$ was added in small portions with stirring, until a clear solution was obtained and a pH value of 6.5–7 was reached. This solution was heated for 6.5 hours in an oil bath at 67° C.; the progress of the reaction can be monitored by TLC (three-days-old CHCl$_3$ 160/MeOH 70/HCOOH 30 or freshly prepared CHCl$_3$ 160/MeOH 10/HCOOH 30 phases; the product has a slightly lower R$_f$ value than the starting material). After cooling at 5° C., a few drops of 8% HCl were carefully added under stirring, causing the separation of a precipitate (at about pH 3). This was collected, washed with acetone (in order to remove excess 1-methyl-5-mercapto-1,2,3,4-tetrazole) and dried, thus giving 70 mg of the title compound, which was identical to that prepared in example 2.

By proceeding analogously also the following compounds were obtained:

7β-[2-(2-imino-3-hydroxy-4-thiazolinyl)-2-methoxy-imino-acetamido]-3-[1-(2-propenyl-1,2,3,4-tetrazol-5-yl)-thiomethyl]-3-cephem-4-carboxylic acid (syn-isomer);

7β-[2-(2-imino-3-hydroxy-4-thiazolinyl)-2-methoxy-imino-acetamido]-3-[1-(2-cyano ethyl-1,2,3,4-tetrazol-5-yl)-thiomethyl]-3-cephem-4-carboxylic acid (syn-isomer);

7β-[2-(2-imino-3-hydroxy-4-thiazolinyl)-2-methoxy-imino-acetamido]-3-[(5-methyl-1,3,4-thiadiazol-2-yl)-thiomethyl]-3-cephem-4-carboxylic acid (syn-isomer);

7β-[2-(2-imino-3-hydroxy-4-thiazolinyl)-2-methoxy-imino-acetamido]-3-[(5-amino-1,3,4-thiadiazol-2-yl)-thiomethyl]-3-cephem-4-carboxylic acid (syn-isomer);

7β-[2-(2-imino-3-hydroxy-4-thiazolinyl)-2-methoxy-imino-acetamido]-3-[(tetrazolo-[1,5-b]-pyridazin-6-yl)-thiomethyl]-3-cephem-4-carboxylic acid (syn-isomer);

7β-[2-(2-imino-3-hydroxy-4-thiazolinyl)-2-methoxy-imino-acetamido]-3-[(8-amino-tetrazolo-[1,5-b]-pyridazin-6-yl)-thiomethyl]-3-cephem-4-carboxylic acid (syn-isomer);

7β-[2-(2-imino-3-hydroxy-4-thiazolinyl)-2-carboxymethoxy-imino-acetamido]-3-[(1-methyl-1,2,3,4-tetrazol-5-yl)-thiomethyl]-3-cephem-4-carboxylic acid (syn-isomer);

7β-[2-(2-imino-3-hydroxy-4-thiazolinyl)-2-carboxymethoxy-imino-acetamido]-3-[(5-methyl-1,3,4-thiadiazol-2-yl)-thiomethyl]-3-cephem-4-carboxylic acid (syn-isomer);

7β-[2-(2-imino-3-hydroxy-4-thiazolinyl)-2-methoxyimino-acetamido]-3-[8-aminocarbonyl-tetrazolo[1,5-b]pyridazin-6-yl-thiomethyl]-3-cephem-4-carboxylic acid (syn-isomer);

7β-[2-(2-imino-3-methoxy-4-thiazolinyl)-2-methoxyimino-acetamido]-3-[8-aminocarbonyl-tetrazolo[1,5-b]pyridazin-6-yl-thiomethyl]-3-cephem-4-carboxylic acid (syn-isomer);

7β-[2-(2-imino-3-amino-4-thiazolinyl)-2-methoxyimino-acetamido]-3-[8-aminocarbonyl-tetrazolo[1,5-b]pyridazin-6-yl-thiomethyl]-3-cephem-4-carboxylic acid (syn-isomer), 7β-[2-(2-imino-3-hydroxy-4-thiazolinyl)-2-methoxy-imino-acetamido]-[(5-methyl mercapto-1,3,4-thiadiazol-2-yl)-thiomethyl]-3-cephem-4-carboxylic acid (syn-isomer);

7β-[2-(2-imino-3-hydroxy-4-thiazolinyl)-2-methoxy-imino-acetamido]-3-[(8-carboxy-tetrazolo[1,5-b]pyridazin-6-yl)-thiomethyl]-3-cephem-4-carboxylic acid (syn-isomer);

7β-[2-(2-imino-3-hydroxy-4-thiazolinyl)-2-methoxy-imino-acetamido]-3-[(8-carboxy methyl-tetrazolo[1,5-b]pyridazin-6-yl)-thiomethyl]-3-cephem-4-carboxylic acid (syn-isomer);

7β-[2-(2-imino-3-hydroxy-4-thiazolinyl)-2-methoxy-imino-acetamido]-3-[(2,3-dihydro-2-methyl-3-oxo-1,2,4-triazolo-(4,3,b)-pyridazin-3-one-6-yl)-thiomethyl]-3-cephem-4-carboxylic acid (syn-isomer);

7β-[2-(2-imino-3-methoxy-4-thiazolinyl)-2-methoxy-imino-acetamido]-3-[(1-methyl-1,2,3,4-tetrazol-5-yl)-thiomethyl]-3-cephem-4-carboxylic acid (syn-isomer);

7β-[2-(2-imino-3-methoxy-4-thiazolinyl)-2-methoxy-imino-acetamido]-3-[1(2-propenyl-1,2,3,4-tetrazol-5-yl)-thiomethyl]-3-cephem-4-carboxylic acid (syn-isomer);

7β-[2-(2-imino-3-methoxy-4-thiazolinyl)-2-methoxy-imino-acetamido]-3-[1-(2-cyanoethyl-1,2,3,4-tetrazol-5-yl)-thiomethyl]-3-cephem-4-carboxylic acid (syn-isomer);

7β-[2-(2-imino-3-methoxy-4-thiazolinyl)-2-methoxy-imino-acetamido]-3-[(5-methyl-1,3,4-thiadiazol-2-yl)-thiomethyl]-3-cephem-4-carboxylic acid (syn-isomer);

7β-[2-(2-imino-3-methoxy-4-thiazolinyl)-2-methoxy-imino-acetamido]-3-[(tetrazolo[1,5-b]pyridazin-6-yl)-thiomethyl]-3-cephem-4-carboxylic acid (syn-isomer);

7β-[2-(2-imino-3-methoxy-4-thiazolinyl)-2-methoxy-imino-acetamido]-3-[(8-amino-tetrazolo[1,5-b]pyridazin-6-yl)-thiomethyl]-3-cephem-4-carboxylic acid (syn-isomer);

7β-[2-(2-imino-3-methoxy-4-thiazolinyl)-2-methoxy-imino-acetamido]-3-[(8-carboxy-tetrazolo[1,5-b]pyridazin-6-yl)-thiomethyl]-3-cephem-4-carboxylic acid (syn-isomer);

7β-[2-(2-imino-3-methoxy-4-thiazolinyl)-2-methoxy-imino-acetamido]-3-[(8-carboxymethyl-tetrazolo[1,5-b]pyridazin-6-yl)-thiomethyl]-3-cephem-4-carboxylic acid (syn-isomer);

7β-[2-(2-imino-3-methoxy-4-thiazolinyl)-2-carboxymethoxy-imino-acetamido]-3-[(1-methyl-1,2,3,4-tetrazol-5-yl)-thiomethyl]-3-cephem-4-carboxylic acid (syn-isomer);

7β-[2-(2-imino-3-methoxy-4-thiazolinyl)-2-carboxymethoxy-imino-acetamido]-3-[(5-methyl-1,3,4-thiadiazol-2-yl)-thiomethyl]-3-cephem-4-carboxylic acid (syn-isomer);

7β-[2-(2-imino-3-methoxy-4-thiazolinyl)-2-carboxymethoxy-imino-acetamido]-3-[(8-amino-tetrazolo[1,5-b]pyridazin-6-yl)-thiomethyl]-3-cephem-4-carboxylic acid (syn-isomer);

7β-[2-(2-imino-3-hydroxy-4-thiazolinyl)-2-(β)carboxy vinylene-oxy-imino-acetamido]-3-[(8-amino-tetrazolo[1,5-b]pyridazin-6-yl)-thiomethyl]-3-cephem-4-carboxylic acid (syn-isomer);

7β-[2-(2-imino-3-amino-4-thiazolinyl)-2-methoxyimino-acetamido]-3-[(1-methyl-1,2,3,4-tetrazol-5-yl)-thiomethyl]-3-cephem-4-carboxylic acid (syn-isomer);

7β-[2-(2-imino-3-amino-4-thiazolinyl)-2-methoxyimino-acetamido]-3-[(5-methyl-1,3,4-thiadiazol-2-yl)-thiomethyl]-3-cephem-4-carboxylic acid (syn-isomer);

7β-[2-(2-imino-3-amino-4-thiazolinyl)-2-methoxyimino-acetamido]-3-[(tetrazolo[1,5-b]pyridazin-6-yl)-thiomethyl]-3-cephem-4-carboxylic acid (syn-isomer);

7β-[2-(2-imino-3-amino-4-thiazolinyl)-2-methoxyimino-acetamido]-3-[(8-amino-tetrazolo[1,5-b]pyridazin-6-yl)-thiomethyl]-3-cephem-4-carboxylic acid (syn-isomer);

7β-[2-(2-imino-3-amino-4-thiazolinyl)-2-carboxymethoxy-imino-acetamido]-3-[(1-methyl-1,2,3,4-tetrazol-5-yl)-thiomethyl]-3-cephem-4-carboxylic acid (syn-isomer);

7β-[2-(2-imino-3-amino-4-thiazolinyl)-2-(β)carboxy vinylene-oxy-imino-acetamido]-3-[(1-methyl-1,2,3,4-tetrazol-5-yl)-thiomethyl]-3-cephem-4-carboxylic acid (syn-isomer).

EXAMPLE 9

7-β-[2-(2-imino-3-hydroxy-4-thiazolinyl)-2-methoxyimino-acetamido]-3-[(1-methyl-1,2,3,4-tetrazol-5-yl)-thiomethyl]-3-cephem-4-carboxylic acid (syn-isomer)

To a solution containing 2-[2-(N-chloroacetyl)-imino-3-hydroxy-4-thiazolinyl]-2-methoxyimino acetic acid (2.3 g) in anhydrous acetone (60 ml) and triethylamine (1.24 ml) cooled at −10° C., isobutylchloroformate (1.7 ml) dissolved in anhydrous acetone (16 ml) was added under stirring. The stirring was continued for 30 minutes at −10° C., then the mixture was cooled at −30° C.

A solution containing 7-amino-3-[(1-methyl-1,2,3,4-tetrazol-5-yl)-thiomethyl]-3-cephem-4-carboxylic acid (2.8 g) and triethylamine (4 ml) in 50% acetone (120 ml) was then added and the resulting mixture was stirred for 1 hour at a temperature between −20° C. and −30° C., subsequently for 1 hour at a temperature between −5° C. to 0° C. and afterwards for 3 hours at room temperature.

The acetone was filtered and evaporated under vacuum; the residue was extracted with ethyl acetate and worked up as reported in example 2, thus giving the title compound, which was identical to that prepared in example 2.

EXAMPLE 10

7β-[2-(2-imino-3-methoxy-4-thiazolinyl)-2-methoxyimino-acetamido]-3-[(1-methyl-1,2,3,4-tetrazol-5-yl)-thiomethyl]-3-cephem-4-carboxylic acid (syn-isomer)

To a solution of 2-[2-(N-chloroacetyl)-imino-3-methoxy-4-thiazolinyl]-2-methoxyimino-acetic acid (3.07 g) in anhydrous THF (120 ml) cooled at −5° C., N,N'-dicyclohexylcarbodiimide (2.06 g) was added. After stirring for 10 minutes at −5° C. and 50 minutes at room temperature, the precipitate dicyclohexylurea was filtered off, and the solution was added into a cooled (−10° C.) solution obtained by stirring 7-amino-3-[(1-methyl-1,2,3,4-tetrazol-5-yl)-thiomethyl]-3-cephem-4-carboxylic acid (3.3 g) and N,O-bis-(trimethylsilyl)-acetamide (8.1 g) in anhydrous THF (200 ml), CH₃CN (80 ml) and DMF (4 ml) for 1 hour at 50° C. The mixture was stirred 20 minutes at −10° C. and 90 minutes at room temperature. H₂O (10 ml) was added in order to hydrolize the silylated product, and the major part of the solvents were evaporated under reduced pressure. The residue was partitioned between H₂O (50 ml) and ethyl acetate (100 ml); the organic layer was separated and the aqueous one was extracted again with ethyl acetate. The combined extracts were dried (Na₂SO₄), concentrated to a small volume and diluted with ethyl ether. The precipitated solid was collected and washed with ethyl ether, thus giving 5.1 g of 7β[2-(2-N-chloroacetyl)-imino-3-methoxy-4-thiazolinyl]-2-methoxyimino-acetamido]-3-[(1-methyl-1,2,3,4-tetrazol-5-yl)-thiomethyl]-3-cephem-4-carboxylic acid. This compound was dissolved in MeCN (200 ml) and heated with diphenyldiazomethane (1.9 g). After stirring 1 hour at room temperature, the solvent was evaporated, the residue was taken up with ethyl acetate, washed with dilute NaHCO₃ solution, then with water, dried (Na₂SO₄), and again evaporated to dryness. The residue was triturated with ethyl ether and filtered, thus affording 6.3 g of benzhydryl ester.

The above-prepared ester was dissolved in DMA (15 ml) and treated with finely grounded thiourea (0.65 g) 2 hours at room temperature. Aqueous NaHCO₃ solution was added under stirring (pH 6.5÷7), the mixture briefly heated at 40° C., then cooled and extracted with ethyl acetate (3×50 cc). The combined organic extracts were washed with water, dried and evaporated. Ethyl ether was added to the oily residue, thus giving after filtration, 4.9 g of the benzhydrylester of the title compound as a slightly yellowish powder.

This ester was added with stirring to ice-cooled trifluoroacetic acid (25 ml). After 30 minutes, TFA was pumped off without external heating. Trituration with ethyl ether and filtration then afforded the trifluoroacetic salt of the title compound, 4.05 g.

This salt was dissolved in anhydrous EtOH (19 ml). With stirring and external cooling, a calculated amount (0.49 ml, 1 equiv.) of pyridine was carefully added. After storing four hours in a refrigerator, the precipitated crystals were collected, washed with ethyl ether and dried, thus giving 2.9 g of the title compound.

Elemental Analysis; Found: C 37.33; H 3.62; N 22.89; S 17.42; Calculated for: $C_{17}H_{19}N_9O_6S_3$: C 37.55; H 3.52; N 23.19; S 17.69.

I.R. (KBr): 1770 cm$^{-1}$ >C=O β-lactam

NMR (d$_6$-DMSO): 3.95 (6H, two s, —CH$_3$ on tetrazole ring and —OCH$_3$ on thiazoline ring), 4.0 (3H, s, =NOCH$_3$), 6.82 (1H, s, 5-H on thiazoline ring), 9.6 (1H, d, —CONH—).

EXAMPLE 11

7β-[2-(2-imino-3-methoxy-4-thiazolinyl)-2-methoxyimino-acetamido]-3-[(8-amino-tetrazolo[1,5-b]-pyridazin-6-yl)-thiomethyl]-3-cephem-4-carboxylic acid (syn-isomer)

To a solution of 7-amino-3-[(tetrazolo 1,5-b pyridazin-8-amino-6-yl)-thiomethyl]-3-cephem-4-carboxylic acid (3.80 g) and NaHCO$_3$ (2 g) in 50% aqueous acetone (60 ml), cooled at 0° C., a solution of 2-[2-(N-chloroacetyl)-imino-3-methoxy-4-thiazolinyl]-2-methoxyimino acetic acid chloride (2.7 g) obtained from the acid by reaction with oxalyl chloride and a few drops of dimethylformamide at 0° C. in acetone (30 ml) was added under stirring. The mixture was stirred for 20 minutes at a temperature between 0° C. and 5° C. The acetone was evaporated, ethyl acetate was added to the resulting aqueous solution which was then acidified with 8% hydrochloric acid to pH 2. The organic phase was washed with water, dried and evaporated under vacuum. The residue was treated with ethyl ether and filtered. The product so obtained was dissolved in N,N-dimethylacetamide and then treated with thiourea as reported in example 2 to give the title compound.

I.R. (KBr): 1760 cm$^{-1}$ >C=O β-lactam

NMR (d$_6$-DMSO): 3.95 (3H,s, —OCH$_3$ on thiazoline ring), 3.99 (3H, s, =NOCH$_3$), 6.41 (1H,s,7-H on pyridazine ring), 7.12 (1H, s, 5-H on thiazoline ring), 7.98 (2H, br-s,—NH$_2$ on pyridazine ring), 9.8 (1H, d, —CONH).

EXAMPLE 12

7β-[2-(2-imino-3-hydroxy-4-thiazolinyl)-2-ethoxyimino-acetamido]-3-[(tetrazolo[1,5-b]pyridazin-6-yl)-thiomethyl]-3-cephem-4-carboxylic acid (syn-isomer) was obtained by using the method reported in Example 2.

Elemental Analysis; Found: C 39.27; H 3.22; N 24.01; S 16.46; Calculated for: $C_{19}H_{18}N_{10}O_6S_3$: C 39.44; H 3.14; N 24.21; S 16.62;

NMR (DMSO-d$_6$): 1.24 (3H, t, —OCH$_2$CH$_3$), 4.22 (2H, q, —OCH$_2$CH$_3$), 7.13 (1H, s, 5-H on thiazoline ring), 7.80 (1H, d, 8-H on the pyridazine ring), 8.64 (1H, d, 7-H on the pyridazine ring), 11.13 (1H, d, —CONH).

I.R. (KBr) cm$^{-1}$ 1770 >C=O β-lactam 1520 —CONH-sec.amide.

EXAMPLE 13

7β-[2-(2-imino-3-hydroxy-4-thiazolinyl)-2-propoxyimino-acetamido]-3-[(tetrazolo[1,5-b]pyridazin-6-yl)-thiomethyl]-3-cephem-4-carboxylic acid (syn-isomer) was prepared by using the method reported in Example 2.

Elemental Analysis; Found: C 40.32; H 3.38; N 23.51; S 16.26; Calculated for: $C_{20}H_{20}N_{10}O_6S_3$: C 40.53; H 3.40; N 23.63; S 16.23.

NMR (DMSO-d$_6$): 0.91 (3H, t, —OCH$_2$CH$_2$CH$_3$), 1.70 (2H, m, —OCH$_2$CH$_2$CH$_3$), 4.20 (2H, t, —OCH$_2$CH$_2$CH$_3$), 7.06 (1H, s, 5-H on thiazoline ring), 7.74 (1H, d, 8-H on the pyridazine ring), 8.55 (1H, d, 7-H on the pyridazine ring), 10.90 (1H, d, —CONH).

I.R. (KBr) cm$^{-1}$ 1770 >C=O β-lactam 1520 —CONH-sec.amide.

EXAMPLE 14

7β-[2-(2-formyl-imino-3-methoxy-4-thiazolinyl)-2-methoxyimino-acetamido]-3-acetoxymethyl-3-cephem-4-carboxylic acid (syn-isomer).

To a solution of 2-[2-(N-formyl)-imino-3-methoxy-4-thiazolinyl]-2-methoxyimino acetic acid (1.09 g) in anhydrous THF (110 ml), cooled at −5° C., N,N'-dicyclohexylcarbodiimide (0.433 g) was added. After stirring for 15 minutes at −5° C. and 40 minutes at room temperature, the precipitated dicyclohexylurea was filtered off and the solution was added into a cooled (−30° C.) solution obtained by stirring 7-amino-3-acetoxymethyl-3-cephem-4-carboxylic acid (0.572 g) and N,O-bis-(trimethyl-silyl)-acetamide (1.02 ml) in anhydrous THF (50 ml) for 1 hour. The mixture was stirred for 20 minutes at −10° C. and 20 minutes at room temperature. The reaction mixture was evaporated to dryness, the residue was taken up with EtOAc and water; the undissolved material was filtered off.

The organic layer was extracted with 5% aqueous NaHCO$_3$ solution; the aqueous phase was washed with ethyl ether, brought to pH 2.5-3 with 23% HCl, saturated with NaCl and extracted with ethyl acetate. The organic layer was washed with saturated aqueous NaCl solution, dried and concentrated to 30 ml, the solid precipitated was filtered, dried thus giving 8.22 g (70%) of the title compound: m.p. 178°-180° C. (dec).

Elemental Analysis; Found: C 41.95; H 3.72; N 13.49; S 12.27; Calculated for: $C_{18}H_{19}N_5O_9S_2$: C 42.10; H 3.73; N 13.63; S 12.49.

NMR (DMSO-d$_6$) 2.05 (3H, s, —OCOCH$_3$), 4.04 (3H, s, =NOCH$_3$), 4.13 (3H, s, =NOCH$_3$), 7.31 (1H, s, 5-H on thiazoline ring), 8.83 (1H, s,

9.93 (1H, d, —CONH).

I.R. (KBr) cm$^{-1}$ 1770 >C=O β-lactam 1520 —CONH-sec.amide.

EXAMPLE 15

7β-[2-(2-imino-3-methoxy-4-thiazolinyl)-2-methoxyiminoacetamido]-3-[(tetrazolo[1,5-b]pyridazin-6-yl)-thiomethyl]-3-cephem-4-carboxylic acid.HCl (syn-isomer).

POCl$_3$ (3.86 ml) was added dropwise to an ice-cold mixture of anhydrous DMF (3.31 ml) and anhydrous ethyl acetate (20 ml). After stirring for 10 minutes at 40° C., the mixture was cooled at 0° C., a solution of 2-(2-formylimino)-3-methoxy-4-thiazolinyl)-2-methoxyimino acetic acid (10.57 g) in THF (200 ml) was then added and the mixture was stirred for 50 minutes at room temperature. At the same time a suspension of 7-amino-3-[(tetrazolo[1,5-b]pyridazin-6-yl)-thiomethyl]-3-cephem-4-carboxylic acid (17.8 g) and N,O-bis-(trimethyl-silyl)-acetamide (41.7 ml) in anhydrous THF (600 ml) and CH₃CN (300 ml) was stirred for 1 hour at 50° C., until all the solid material was dissolved.

Into this solution, cooled with an ice-bath, the first solution was dropped with stirring. After stirring for 90 minutes at 20° C., the reaction mixture was evaporated to dryness under vacuum; the residue was taken up with ethyl acetate; the undissolved matter was filtered off. The organic phase was extracted with 5% aqueous NaHCO₃ solution; the organic phase was brought to pH 3 with 23% HCl, and extracted with ethyl acetate. The organic layer was dried and evaporated to dryness. The residue was crystallized from ethyl acetate thus giving 16.1 g (65%) of 7β-[2-(2-formylimino-3-methoxy-4-thiazolinyl)-2-methoxyimino-acetamido]-3-[(tetrazolo[1,5-b]pyridazin-6-yl)-thiomethyl]-3-cephem-4-carboxylic acid (syn-isomer).

Elemental Analysis; Found: C 39.45; H 3.10; N 22.98; S 15.77; Calculated for: C₂₀H₁₈N₁₀O₇S₃: C 39.60; H 2.99; N 23.09; S 15.86.

NMR (DMSO-d₆): 4.03 and 4.12 (6H, 2s, =NOCH₃ and >N—OCH₃), 7.29 (1H, s, 5-H on thiazoline ring), 7.80 (1H, d, 8-H on the pyridazine ring), 8.64 (1H, d, 7-H on the pyridazine ring), 9.91 (1H, d, —CONH).

This compound (9.2 g) was added to an ice-cold solution of POCl₃ (1.73 ml) in CH₃OH (740 ml) and the mixture was stirred for 2 hours at room temperature.

After evaporating to dryness the residue was triturated with fresh ethyl acetate until a powder was obtained.

The product was collected by filtration thus giving 9.1 g (97%) of the title compound: m.p. 200° C. (dec.).

Elemental Analysis; Found: C 37.22; H 3.06; N 22.61; S 15.49; Calculated for: C₁₉H₁₉ClN₁₀O₆S₃: C 37.10; H 3.11; N 22.77; S 15.64.

NMR (DMSO-d₆): 4.04 and 4.10 (6H, 2s, =NOCH₃ and >NOCH₃), 7.20 (1H, s, 5-H on thiazoline ring), 7.83 (1H, d, 8-H on the pyridazine ring), 8.66 (1H, d, 7-H on the pyridazine ring), 9.98 (1H, d, —CONH).

I.R. (KBr) cm⁻¹ 1770 C=O β-lactam 1520 —CONH sec.amide.

EXAMPLE 16

7β-[2-(2-N-chloroacetylimino-3-isopropylideneamino-4-thiazolinyl)-2-methoxyimino-acetamido]-3-acetoxymethyl-3-cephem-4-carboxylic acid (syn-isomer).

A solution of N,N'-dicyclohexylcarbodiimide (0.693 g) in THF (25 ml) was added to a suspension of 2-(2-chloroacetylimino)-3-isopropylideneamino-4-thiazolinyl)-2-methoxyimino acetic acid (1.5 g) and 7-ACA tert.butyl ester (1.22 g) in acetone (20 ml) and THF (20 ml).

After stirring for 15 minutes at room temperature, the insoluble matter was filtered off, the filtrate evaporated to dryness, the residue chromatographed on silica gel using ligroin; acetone (100:50) as eluent.

The normal work-up afforded 2.02 g (70%) of the tert.butyl ester of the title compound: m.p.=179° C. (dec.).

Elemental Analysis; Found: C 46.81; H 5.06; Cl 5.44; N 12.93; S 9.61; Calculated for: C₂₅H₃₁ClN₆O₈S₂: C 46.68; H 4.85; Cl 5.51; N 13.06; S 9.97.

NMR (DMSO-d₆): 1.58 (9H, s, —OC(CH₃)₃), 1.97 and 2.12 (6H, 2s,

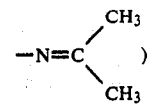

2.29 (3H, s, —OCOCH₃), 4.17 (3H, s, =NOCH₃), 4.28 (2H, s, —COCH₂Cl), 7.09 (1H, s, 5-H on thiazoline ring), 7.80 (1H, d, —CONH).

The above-prepared ester was treated with trifluoroacetic acid and anisole in acetone for 30 minutes at room temperature. After normal work-up, 0.57 g (65%) of the title compound was obtained, m.p. 125°–130° C.

Elemental analysis; Found: C 42.71; H 3.81; Cl 5.99; N 14.22; S 10.83; calculated for C₂₁H₂₃ClN₆O₈S₂: C 42.96; H 3.95; Cl 6.03; N 14.32; S 10.92.

N.M.R. (DMSO-d₆): 1.83 and 2.25 (6H, s,

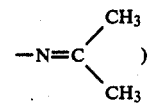

2.06 (3H, s, —OCOCH₃), 3.98 (3H, s, =NOCH₃), 4.36 (2H, s, —COCH₂Cl), 7.46 (1H, s, 5-H on thiazoline ring), 9.84 (1H, d, —CONH).

I.R. (KBr) cm⁻¹ 1770 >C=O β-lactam 1520 —CONH— sec. amide

EXAMPLE 17

7β-[2-(2-chloroacetylimino-3-amino-4-thiazolinyl)-2-methoxyimino-acetamido]-3-acetoxymethyl-3-cephem-4-carboxylic acid (syn-isomer)

To a stirred suspension of the compound 7β-[2-(2-N-chloroacetylimino-3-isopropylideneamino-4-thiazolinyl)-2-methoxyimino-acetamido]-3-acetoxymethyl-3-cephem-4-carboxylic acid (syn-isomer) (0.3 g) in dimethylsulphoxide (0.55 ml), water (0.4 ml) was added slowly in 90 minutes; each addition of water caused the separation of a precipitate, which then dissolved under stirring. The reaction mixture was then diluted with water (20 ml) and stirred so obtaining a solid which was filtered, washed with water and dried thus giving 0.205 g of the title compound, m.p. 116° C.

Elemental analysis; Found: C 39.60; H 3.69; Cl 6.34; N 15.12; S 11.56; calculated for C₁₈H₁₉ClN₆O₈S₂: C 39.52; H 3.50; Cl 6.48; N 15.36; S 11.72;

N.M.R. (CF₃COOD): 2.06 (3H, s, —OCOCH₃), 4.04 (3H, s, =NOCH₃), 4.42 (2H, s, —COCH₂Cl), 6.25 (2H, br-s, —NH₂), 7.32 (1H, s, 5-H on thiazoline ring), 9.68 (1H, d, —CONH).

EXAMPLE 18

7β-[2-(2-imino-3-isopropylideneamino-4-thiazolinyl)-2-methoxyimino-acetamido]-3-acetoxymethyl-3-cephem-4-carboxylic acid.HCl (syn-isomer)

A solution of the compound prepared in example 16 (0.27 g) and thiourea (0.035 g) in N,N-dimethylacetamide (0.5 ml) was stirred for 2 hours at room temperature. The solution was then diluted with ethyl acetate; a gummy material precipitated, the supernatant solvent was discarded and the residue was carefully triturated with fresh ethyl acetate until a powder was obtained. The product was collected by filtration, washed with ethyl acetate then with ethyl ether, dried, thus giving 182 mg (70%) of the title compound, m.p. 120° C. (dec.).

Elemental analysis; Found: C 41.64; H 4.31; Cl 6.33; N 15.11; S 11.53; calculated for $C_{19}H_{23}ClN_6O_7S_2$: C 41.71; H 4.23; Cl 6.48; N 15.36; S 11.72;

T.L.C. ($CHCl_3:CH_3OH:HCOOH = 160:60:20$): $R_f = 0.48$

N.M.R. (DMSO-$d_6$): 1.98 and 2.05 (6H, 2s,

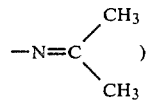

2.26 (3H, s, —OCOCH$_3$), 3.96 (3H, s, =NOCH$_3$), 7.34 (1H, s, 5-H on thiazoline ring), 9.94 (1H, d, —CONH).

EXAMPLE 19

7β-[2-(2-imino-3-amino-4-thiazolinyl)-2-methoxyimino-acetamido]-3-acetoxymethyl-3-cephem-4-carboxylic acid.HCl (syn-isomer)

A solution of the compound prepared in example 17 (1.2 g) and thiourea (0.170 g) in N,N-dimethylacetamide (2.4 ml) was stirred for 4 hours at room temperature. The solution was then diluted with ethyl acetate. The solid precipitated was filtered, washed with ethyl acetate, dried. The crude product was dissolved in ethanol (300 ml) at 45° C., ethyl acetate (400 ml) was added. The solid was filtered, washed with ethyl ether, dried, thus giving 0.84 g (75%) of the title compound, m.p. 160° C. (dec.).

Elemental analysis; Found: C 37.71; H 3.61; Cl 6.71; N 16.43; S 12.41; calculated for $C_{16}H_{19}ClN_6O_7S_2$: C 37.90; H 3.77; Cl 6.99; N 16.58; S 12.65.

T.L.C. ($CHCl_3: CH_3OH:HCOOH = 160:60:20$): $R_f = 0.29$

N.M.R. (DMSO-$d_6$): 2.05 (3H, s, —OCOCH$_3$), 4.07 (3H, s, =NOCH$_3$), 6.15 (2H, br-s, —NH$_2$), 7.14 (1H, s, 5-H on thiazoline ring), 9.53 (1H, d, —CONH).

EXAMPLE 20

To an aqueous suspension of 7β-[2-(2-imino-3-hydroxy-4-thiazolinyl)-2-methoxy-imino-acetamido]-3-[(tetrazolo[1,5-b]pyridazin-6-yl)-thiomethyl]-3-cephem-4-carboxylic acid (syn-isomer) (5.65 g) in water (80 ml), the stoichiometric amount of NaHCO$_3$ was added, so obtaining the complete solution of the compound. This solution was then lyophilized so obtaining the sodium salt of 7β-[2-(2-imino-3-hydroxy-4-thiazolinyl)-2-methoxy-imino-acetamido]-3-[(tetrazolo[1,5-b]pyridazin-6-yl)-thiomethyl]-3-cephem-4-carboxylic acid (syn-isomer).

Elemental analysis; Found: Na 3.81; calculated Na 3.92.

I.R. (KBr) 1770 cm$^{-1}$ >C=O (β-lactam)

EXAMPLE 21

To a solution of 7β-[2-(2-imino-3-hydroxy-4-thiazolinyl)-2-methoxy-imino-acetamido]-3-[(tetrazolo[1,5-b]pyridazin-6-yl)-thiomethyl]-3-cephem-4-carboxylic acid (syn-isomer) (5.65 g) in acetone (400 ml), the stoichiometric amount of a 30% solution of sodium 2-ethyl-hexanoate in isopropyl alcohol was added. After stirring for 30 minutes at room temperature, the mixture was diluted with petroleum ether and the obtained precipitate was filtered to give the sodium salt of 7β-[2-(2-imino-3-hydroxy-4-thiazolinyl)-2-methoxy-imino-acetamido]-3-[(tetrazolo[1,5-b]pyridazin-6-yl)-thiomethyl]-3-cephem-4-carboxylic acid (syn-isomer).

Elemental analysis; Found: Na 3.82; calculated: Na 3.92.

I.R. (KBr) 1770 cm$^{-1}$ >C=O (β-lactam)

EXAMPLE 22

An injectable pharmaceutical composition was performed by dissolving 100–500 mg of sodium salt of 7β-[2-(2-imino-3-hydroxy-4-thiazolinyl)-2-methoxy-imino-acetamido]-3-[(tetrazolo[1,5-b]pyridazin-6-yl)-thiomethyl]-3-cephem-4-carboxylic acid (syn-isomer) in sterile water or sterile normal saline solution (1–2 ml).

We claim:

1. Compound of the formula (I)

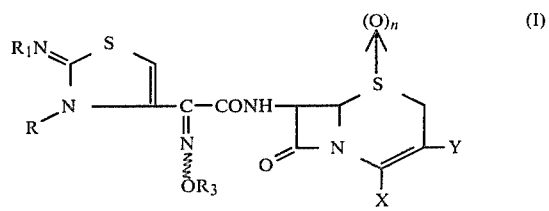

wherein

R is (1) —OR$_2$ in which R$_2$ is a hydrogen atom or a saturated or unsaturated C$_1$-C$_6$ branched or straight chain aliphatic hydrocarbon group which is unsubstituted or substituted by a substituent selected from the group consisting (a) cyano; (b) -COOR$_4$ in which R$_4$ is hydrogen, or C$_1$-C$_6$ alkyl and (c)

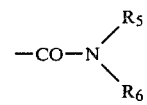

in which each of the groups R$_5$ and R$_6$, which may be the same or different, represents a hydrogen atom, a C$_1$-C$_6$ alkyl or a C$_2$-C$_6$ alkanoyl group or (2)

wherein R$_5$ and R$_6$ are as defined above;

R$_1$ represents a hydrogen atom;

R$_3$ represents a hydrogen atom, or a branched or straight chain saturated or unsaturated C$_1$-C$_6$ aliphatic hydrocarbon group, which may be unsubstituted or substituted by one or more substituents selected from (a') hydroxy; (b') cyano; (c') C$_1$-C$_6$ alkyl, (d')

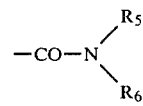

in which R$_5$ and R$_6$ are as defined above; (e') -COOR$_7$ in which R$_7$ may be hydrogen, C$_1$-C$_6$ alkyl, aryl, indanyl, or acetoxymethyl, or (f') halo-$C_1$-$C_6$ alkyl;

n is zero, 1 or 2;

Y is hydrogen; halogen; hydroxy; $C_1$-$C_6$ alkoxy; $C_1$-$C_6$ alkyl or a group —$CH_2$—Z is which Z is (1)

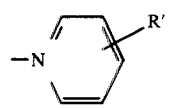

or (2)

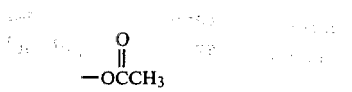

where R' is hydrogen, $C_1$-$C_6$ alkyl, carboxy, cyano or carbamoyl; or (3) —S—Het, wherein Het is:

(1) a tetrazolyl radical, unsubstituted or substituted by $C_1$-$C_3$ alkyl, $C_2$-$C_4$ alkenyl, $(CH_2)_{m_1}$—$COOR_4$ wherein $m_1$ is 1, 2 or 3 and $R_4$ is as defined above, —CH=CH—$COOR_4$ wherein $R_4$ is as defined above, $(CH_2)_{m_1}$—CN; $(CH_2)_{m_1}$—$CONH_2$ or $(CH_2)_{m_1}$—$SO_3H$ wherein $m_1$ is as defined above,

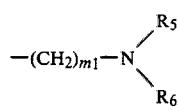

wherein $m_1$ is as defined above and $R_5$ and $R_6$ are as defined above;

(2) a thiadiazolyl radical, unsubstituted or substituted by $C_1$-$C_4$ alkyl, $C_2$-$C_4$ alkenyl, —SH; —$SCH_3$, —$SCH_2COOH$, $(CH_2)_m$—COOH,

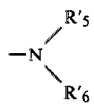

wherein each of R'$_5$ and R'$_6$ is hydrogen or $C_1$-$C_3$ alkyl and m is 0, 1, 2 or 3;

(3) a heterobicyclic ring selected from tetrazolopyridazinyl, tetrazolopyrazinyl, thiadiazolopyridazinyl, and triazolopyridazinyl, each optionally substituted by hydroxy, —SH,

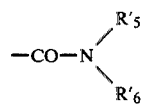

wherein R'$_5$ and R'$_6$ are as defined above, —$COOR_4$ wherein $R_4$ is as defined above, $C_1$-$C_3$ alkyl, $C_2$-$C_4$ alkenyl, —S—$CH_2COOR_4$, —$CH_2COOR_4$, or —CH=CH—$COOR_4$, wherein $R_4$ is as defined above; or

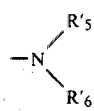

wherein R'$_5$ and R'$_6$ are as defined above; and

X is a free carboxy group or a pharmaceutically acceptable ester thereof; and the pharmaceutically and veterinarily acceptable salts thereof.

2. Compounds of claim 1, wherein $R_1$ is hydrogen;

R is —hydroxy; —O—$C_1$-$C_6$ alkyl; —O—$C_2$-$C_4$ alkenyl; —O—$(CH_2)_{m_1}$—$COOR_4$, wherein $m_1$ and $R_4$ are as defined in claim 1; amino; —$NHCH_3$; —$N(CH_3)_2$ or

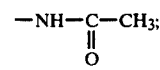

$R_3$ is hydrogen, $C_1$-$C_6$ alkyl, $C_2$-$C_4$ alkenyl, $(CH_2)_{m_1}$—COOH

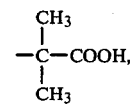

$(CH_2)_{m_1}$—CN, $(CH_2)_{m_1}$—$CONH_2$ wherein $m_1$ is as defined above; or —CH=CH—COOH;

Y is hydrogen, halogen, hydroxy, $C_1$-$C_6$ alkoxy, methyl,

or $CH_2$—S—HET, wherein HET is as defined in claim 1;

n is zero;

X is a free carboxy group, and the pharmaceutically and veterinarily acceptable salts thereof.

3. Syn-isomer of the compound of claim 1, wherein $R_1$ is hydrogen;

R is hydroxy, —O—$C_1$-$C_6$ alkyl, amino;

$R_3$ is hydrogen; $C_1$-$C_6$ alkyl; $C_2$-$C_4$ alkenyl; $(CH_2)_{m_1}$—COOH wherein $m_1$ is as defined in claim 1,

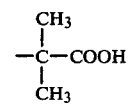

or —CH=CH—COOH;

Y is hydrogen, halogen, hydroxy, methoxy, methyl,

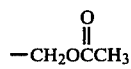

or $CH_2$—S—Het, wherein Het is (1) tetrazolyl unsubstituted or substituted by $C_1$-$C_3$ alkyl, $C_2$-$C_4$ alkenyl, $(CH_2)_{m_1}$—COOH, $(CH_2)_{m_1}$—CN or

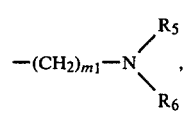

wherein $m_1$ is as defined above and $R_5$ and $R_6$ are independently hydrogen, $C_1$-$C_6$ alkyl or $C_2$-$C_6$ alkanoyl (2) a thiadiazolyl radical, unsubstituted or substituted by methyl, C$_2$–C$_4$ alkenyl; —SH; —SCH$_3$; —SCH$_2$COOH; —(CH$_2$)$_m$—COOH;

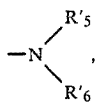

wherein R'$_5$ and R'$_6$ are independently hydrogen or C$_1$–C$_3$ alkyl and m is as defined in claim 1; (3) tetrazolopyridazinyl, optionally substituted by hydroxy, —SH,

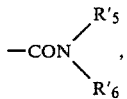

wherein R'$_5$ and R'$_6$ are as defined above; —COOR$_4$ wherein R$_4$ is as defined in claim 15; C$_1$–C$_3$ alkyl; C$_2$–C$_4$ alkenyl; —CH$_2$COOR$_4$ or —CH=CH—COOR$_4$, wherein R$_4$ is as defined above or

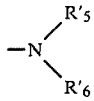

wherein R'$_5$ and R'$_6$ are as defined above;
n is zero;
X is a free carboxy group, and the pharmaceutically and veterinarily acceptable salts thereof.
4. Syn-isomer of the compound of claim 1, wherein
R$_1$ is hydrogen;
R is hydroxy;
R$_3$ is hydrogen, C$_1$–C$_6$ alkyl, C$_2$–C$_4$ alkenyl, —(CH$_2$)m$_1$—COOH wherein m$_1$ is 1, 2 or 3,

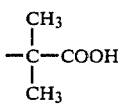

or —CH=CH—COOH;
Y is hydrogen, halogen, hydroxy, methoxy,

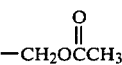

or —CH$_2$—S—Het, wherein Het is (1) tetrazolyl unsubstituted or substituted by C$_1$–C$_3$ alkyl, C$_2$–C$_4$ alkenyl, —(CH$_2$)m$_1$—COOH, —(CH$_2$)m$_1$—CN or

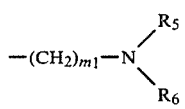

wherein m$_1$ is as defined above and R$_5$ and R$_6$ are independently hydrogen, C$_1$–C$_6$ alkyl or C$_2$–C$_4$ alkanoyl; (2) a thiadiazolyl radical, unsubstituted or substituted by methyl, C$_2$–C$_4$ alkenyl; —SH; —SCH$_3$; —SCH$_2$COOH; —(CH$_2$)$_m$—COOH;

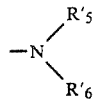

wherein m, R'$_5$ and R'$_6$ are as defined in claim 1; (3) tetrazolopyridazinyl, optionally substituted by hydroxy, —SH,

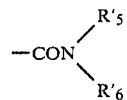

wherein R'$_5$ and R'$_6$ are as defined above; —COOR$_4$ wherein R$_4$ is as defined in claim 15; C$_1$–C$_3$ alkyl; C$_2$–C$_4$ alkenyl, —CH$_2$COOR$_4$ or —CH=CH—COOR$_4$, wherein R$_4$ is as defined above or

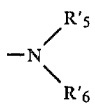

wherein R'$_5$ and R'$_6$ are as defined above
n is zero;
X is a free carboxy group, and the pharmaceutically and veterinarily acceptable salts thereof.
5. 7β-[2-(2-imino-3-hydroxy-4-thiazolinyl)-2-methoxy-imino-acetamido]-3-[(tetrazolo[1,5-b]pyridazin-6-yl)-thiomethyl]-3-cephem-4-carboxylic acid and its pharmaceutically and veterinarily acceptable salts and esters.
6. 7β-[2-(2-imino-3-hydroxy-4-thiazolinyl)-2-methoxy-imino-acetamido]-3-[(tetrazolo[1,5-b]pyridazin-6-yl)-thiomethyl]-3-cephem-4-carboxylic acid (syn-isomer) and its pharmaceutically and veterinarily acceptable salts and esters.
7. A compound selected from
7β-[2-(2-imino-3-hydroxy-4-thiazolinyl)-2-hydroxy-imino-acetamido]-3-cephem-4-carboxylic acid (syn-isomer);
7β-[2-(2-imino-3-hydroxy-4-thiazolinyl)-2-methoxy-imino-acetamido]-3-cephem-4-carboxylic acid (syn-isomer);
7β-[2-(2-imino-3-hydroxy-4-thiazolinyl)-2-methoxy-imino-acetamido]-1(R)-sulphoxide-3-cephem-4-carboxylic acid (syn-isomer);
7β-[2-(2-imino-3-hydroxy-4-thiazolinyl)-2-methoxy-imino-acetamido]-1(S)-sulphoxide-3-cephem-4-carboxylic acid (syn-isomer);
7β-[2-(2-imino-3-hydroxy-4-thiazolinyl)-2-methoxy-imino-acetamido]-3-chloro-3-cephem-4-carboxylic acid (syn-isomer);
7β-[2-(2-imino-3-hydroxy-4-thiazolinyl)-2-methoxy-imino-acetamido]-3-hydroxy-3-cephem-4-carboxylic acid (syn-isomer);
7β-[2-(2-imino-3-hydroxy-4-thiazolinyl)-2-methoxy-imino-acetamido]-3-methoxy-3-cephem-4-carboxylic acid (syn-isomer);
7β-[2-(2-imino-3-hydroxy-4-thiazolinyl)-2-methoxy-imino-acetamido]-3-acetoxy-methyl-3-cephem-4-carboxylic acid; (syn-isomer);

7β-[2-(2-imino-3-hydroxy-4-thiazolinyl)-2-methoxy-imino-acetamido]-1(R)-sulphoxide-3-acetoxymethyl-3-cephem-4-carboxylic acid (syn-isomer);

7β-[2-(2-imino-3-hydroxy-4-thiazolinyl)-2-methoxy-imino-acetamido]-1(S)-sulphoxide-3-acetoxy-methyl-3-cephem-4-carboxylic acid (syn-isomer);

7β-[2-(2-imino-3-hydroxy-4-thiazolinyl)-2-methoxy-imino-acetamido]-3-[-(1-methyl-1,2,3,4-tetrazol-5-yl)-thiomethyl]-3-cephem-4-carboxylic acid (syn isomer);

7β-[2-(2-imino-3-hydroxy-4-thiazolinyl)-2-methoxy-imino-acetamido]-3-[1-(2-propenyl)-1,2,3,4-tetrazol-5-yl)-thiomethyl]-3-cephem-4-carboxylic acid (syn isomer);

7β-[2-(2-imino-3-hydroxy-4-thiazolinyl)-2-methoxy-imino-acetamido]-3-(1-[2-cyanoethyl]-1,2,3,4-tetrazol-5-yl)-thiomethyl]-3-cephem-4-carboxylic acid (syn isomer);

7β-[2-(2-imino-3-hydroxy-4-thiazolinyl)-2-methoxy-imino-acetamido]-3-[(5-methyl-1,3,4-thiadiazol-2-yl)-thiomethyl]-3-cephem-4-carboxylic acid (syn isomer);

7β-[2-(2-imino-3-hydroxy-4-thiazolinyl)-2-methoxy-imino-acetamido]-3-[(5-methyl-mercapto-1,3,4-thiadiazol-2-yl)-thiomethyl]-3-cephem-4-carboxylic acid (syn isomer);

7β-[2-(2-imino-3-hydroxy-4-thiazolinyl)-2-methoxy-imino-acetamido]-3-[(5-amino-1,3,4-thiadiazol-2-yl)-thiomethyl]-3-cephem-4-carboxylic acid (syn isomer);

7β-[2-(2-imino-3-hydroxy-4-thiazolinyl)-2-methoxy-imino-acetamido]-3-[(8-amino-tetrazolo[1,5-b]pyridazin-6-yl)-thiomethyl]-3-cephem-4-carboxylic acid (syn isomer);

7β-[2-(2-imino-3-hydroxy-4-thiazolinyl)-2-methoxy-imino-acetamido]-3-[(8-carboxy-tetrazolo[1,5-b]pyridazin-6-yl)-thiomethyl]-3-cephem-4-carboxylic acid (syn isomer);

7β-[2-(2-imino-3-hydroxy-4-thiazolinyl)-2-methoxy-imino-acetamido]-3-[(8-carboxy-methyl-tetrazolo[1,5-b]pyridazin-6-yl)-thiomethyl]-3-cephem-4-carboxylic acid (syn isomer);

7β-[2-(2-imino-3-hydroxy-4-thiazolinyl)-2-methoxy-imino-acetamido]-3-[(2,3dihydro-2-methyl-3-oxo-1,2,4-triazolo-[4,3,b]-pyridazin-6-yl)-thiomethyl]-3-cephem-4-carboxylic acid (syn isomer);

7β-[2-(2-imino-3-hydroxy-4-thiazolinyl)-2-carboxymethoxy-imino-acetamido]-3-[(1-methyl-1,2,3,4-tetrazol-5-yl)-thiomethyl]-3-cephem-4-carboxylic acid (syn isomer);

7β-[2-(2-imino-3-hydroxy-4-thiazolinyl)-2-carboxymethoxy-imino-acetamido]-3-[(5-methyl-1,3,4-thiadiazol-2-yl)-thiomethyl]-3-cephem-4-carboxylic acid (syn isomer);

7β-[2-(2-imino-3-hydroxy-4-thiazolinyl)-2-carboxymethoxy-imino-acetamido]-3-[(8-amino-tetrazolo[1,5-b]pyridazin-6-yl) -thiomethyl]-3-cephem-4-carboxylic acid (syn isomer);

7β-[2-(2-imino-3-hydroxy-4-thiazolinyl)-2-(β-carboxyvinyleneoxy-imino)-acetamido]-3-[(8-amino-tetrazolo[1,5-b]pyridazin-6-yl)-thiomethyl]-3-cephem-4-carboxylic acid (syn isomer);

7β-[2-(2-imino-3-hydroxy-4-thiazolinyl)-2-methoxy-imino-acetamido]-1-sulphone-3-cephem-4-carboxylic acid (syn isomer);

7β-[2-(2-imino-3-hydroxy-4-thiazolinyl)-2-methoxy-imino-acetamido]-1-sulphone-3-acetoxy methyl-3-cephem-4-carboxylic acid (syn isomer);

7β-[2-(2-imino-3-hydroxy-4-thiazolinyl)-2-(α-methyl-α-carboxy-ethoxyimino)-acetamido]-3-acetoxymethyl-3-cephem-4-carboxylic acid (syn isomer);

7β-[2-(2-imino-3-hydroxy-4-thiazolinyl)-2-methoxyimino-acetamido]-3-[8-aminocarbonyl-tetrazolo[1,5-b]pyridazin-6-yl-]thiomethyl]-3-cephem-4-carboxylic acid (syn-isomer);

and the pharmaceutically and veterinarily acceptable salts and esters thereof.

8. A compound selected from

7β-[2-(2-imino-3-methoxy-4-thiazolinyl)-2-methoxyimino-acetamido]-3-cephem-4-carboxylic acid (syn-isomer);

7β-[2-(2-imino-3-methoxy-4-thiazolinyl)-2-methoxyimino-acetamido]-3-acetoxy-methyl-3-cephem-4-carboxylic acid (syn isomer);

7β-[2-(2-imino-3-methoxy-4-thiazolinyl)-2-methoxyimino-acetamido]-1(R)-sulphoxide-3-acetoxymethyl-3-cephem-4-carboxylic acid (syn isomer);

7β-[2-(2-imino-3-methoxy-4-thiazolinyl)-2-methoxyimino-acetamido]-1(S)-sulphoxide-3-acetoxy-methyl-3-cephem-4-carboxylic acid (syn isomer);

7β-[2-(2-imino-3-methoxy-4-thiazolinyl)-2-methoxyimino-acetamido]-3-[(1-methyl-1,2,3,4-tetrazol-5-yl)-thiomethyl]-3-cephem-4-carboxylic acid (syn-isomer);

7β-[2-(2-imino-3-methoxy-4-thiazolinyl)-2-methoxyimino-acetamido]-3-(1-[2-propenyl]-1,2,3,4-tetrazol-5-yl)-thiomethyl]-3-cephem-4-carboxylic acid (syn isomer);

7β-[2-(2-imino-3-methoxy-4-thiazolinyl)-2-methoxyimino-acetamido]-3-[1-cyanoethyl-1,2,3,4-tetrazol-5-yl)-thiomethyl]-3-cephem-4-carboxylic acid (syn-isomer);

7β-[2-(2-imino-3-methoxy-4-thiazolinyl)-2-methoxyimino-acetamido]-3-[(5-methyl-1,3,4-thiadiazol-2-yl)-thiomethyl]-3-cephem-4-carboxylic acid (syn-isomer);

7β-[2-(2-imino-3-methoxy-4-thiazolinyl)-2-methoxyimino-acetamido]-3-[(tetrazolo[1,5-b]pyridazin-6-yl)-thiomethyl]-3-cephem-4-carboxylic acid (syn-isomer);

7β-[2-(2-imino-3-methoxy-4-thiazolinyl)-2-methoxyimino-acetamido]-3-[(8-amino-tetrazolo[1,5-b]pyridazin-6-yl)-thiomethyl]-3-cephem-4-carboxylic acid (syn-isomer);

7β-[2-(2-imino-3-methoxy-4-thiazolinyl)-2-methoxyimino-acetamido]-3-[(8-carboxy-tetrazolo[1,5-b]pyridazin-6-yl)-thiomethyl]-3-cephem-4-carboxylic acid (syn-isomer);

7β-[2-(2-imino-3-methoxy-4-thiazolinyl)-2-methoxyimino-acetamido]-3-[(8-carboxymethyl-tetrazolo[1,5-b]pyridazin-6-yl)-thiomethyl]-3-cephem-4-carboxylic acid (syn-isomer);

7β-[2-(2-imino-3-methoxy-4-thiazolinyl)-2-carboxymethoxy-imino-acetamido]-3-[(1-methyl-1,2,3,4-tetrazol-5-yl)-thiomethyl]-3-cephem-4-carboxylic acid (syn isomer);

7β-[2-(2-imino-3-methoxy-4-thiazolinyl)-2-carboxymethoxy-imino-acetamido]-3-[(5-methyl-1,3,4-thiadiazol-2-yl)-thiomethyl]-3-cephem-4-carboxylic acid (syn isomer);

7β-[2-(2-imino-3-methoxy-4-thiazolinyl)-2-carboxymethoxy-imino-acetamido]-3-[(8-amino-tetrazolo[1,5-b]pyridazin-6-yl)-thiomethyl]-3-cephem-4-carboxylic acid (syn isomer);

7β-[2-(2-imino-3-methoxy-4-thiazolinyl)-2-methoxy-imino-acetamido]-1-sulphone-3-acetoxymethyl-3-cephem-4-carboxylic acid (syn isomer);

7β-[2-(2-imino-3-methoxy-4-thiazolinyl)-2-(α-methyl-α-carboxy-ethoxy-imino)-acetamido]-3-acetoxymethyl-3-cephem-4-carboxylic acid (syn isomer);

7β-[2-(2-imino-3-methoxy-4-thiazolinyl)-2-methoxy-imino-acetamido]-3-[8-aminocarbonyl-tetrazolo[1,5-b]pyridazin-6-ylthiomethyl]-3-cephem-4-carboxylic acid (syn-isomer);

and the pharmaceutically and veterinarily acceptable salts and esters thereof.

9. A compound selected from

7β-[2-(2-imino-3-amino-4-thiazolinyl)2-methoxy-imino-acetamido]-3-cephem-4-carboxylic acid (syn-isomer);

7β-[2-(2-imino-3-amino-4-thiazolinyl)-2-methoxy-imino-acetamido]-3-acetoxy-methyl-3-cephem-4-carboxylic acid (syn-isomer);

7β-[2-(2-imino-3-amino-4-thiazolinyl)-2-methoxy-imino-acetamido]-1(R)-sulphoxide-3-acetoxymethyl-3-cephem-4-carboxylic acid (syn isomer);

7β-[2-(2-imino-3-amino-4-thiazolinyl)-2-methoxy-imino-acetamido]-1(S)-sulphoxide-3-acetoxy-methyl-3-cephem-4-carboxylic acid (syn-isomer);

7β-[2-(2-imino-3-amino-4-thiazolinyl)-2-methoxy-imino-acetamido]-3-[(1-methyl-1,2,3,4-tetrazol-5-yl)-thiomethyl]-3-cephem-4-carboxylic acid (syn isomer);

7β-[2-(2-imino-3-amino-4-thiazolinyl)-2-methoxy-imino-acetamido]-3-[(5-methyl-1,3,4-thiadiazol-2-yl)-thiomethyl]-3-cephem-4-carboxylic acid (syn isomer);

7β-[2-(2-imino-3-amino-4-thiazolinyl)-2-methoxy-imino-acetamido]-3-[(tetrazolo[1,5-b]pyridazin-6-yl)-thiomethyl]-3-cephem-4-carboxylic acid (syn isomer);

7β-[2-(2-imino-3-amino-4-thiazolinyl)-2-methoxy-imino-acetamido]-3-[(8-amino-tetrazolo[1,5-b]pyridazin-6-yl)-thiomethyl]-3-cephem-4-carboxylic acid (syn isomer);

7β-[2-(2-imino-3-amino-4-thiazolinyl)-2-carboxymethoxy-imino-acetamido]-3-[(1-methyl-1,2,3,4-tetrazol-5-yl)-thiomethyl]-3-cephem-4-carboxylic acid (syn isomer);

7β-[2-(2-imino-3-amino-4-thiazolinyl)-2-(β-carboxyvinyleneoxy-imino)-acetamido]-3-[(1-methyl-1,2,3,4-tetrazol-5-yl)-thiomethyl]-3-cephem-4-carboxylic acid (syn isomer);

7β-[2-(2-imino-3-amino-4-thiazolinyl)-2-methoxy-imino-acetamido]-1-sulphone-3-acetoxymethyl-3-cephem-4-carboxylic acid (syn isomer);

7β-[2-(2-imino-3-amino-4-thiazolinyl)-2-(β-methyl-α-carboxyethoxyimino)-acetamido]-3-acetoxymethyl-3-cephem-4-carboxylic acid (syn-isomer);

7β-[2-(2-imino-3-amino-4-thiazolinyl)-2-methoxyimino-acetamido]-3-[8-aminocarbonyl-tetrazolo[1,5-b]pyridazin-6-ylthiomethyl]-3-cephem-4-carboxylic acid (syn-isomer), and the pharmaceutically and veterinarily acceptable salts and esters thereof.

10. An anti-bacterial pharmaceutical or veterinary composition containing an effective amount of a compound of any one of claims 5 to 9, or 1 to 4 and a pharmaceutically or veterinarily acceptable carrier or diluent.

11. A method of treating bacterial infection in a patient in need of such treatment, said method comprising administering to said patient an anti-bacterial amount of a compound of any one of claims 5 to 9 or 1 to 4.

* * * * *